United States Patent
Barr et al.

(10) Patent No.: US 12,338,223 B2
(45) Date of Patent: Jun. 24, 2025

(54) METHODS OF PREPARING SYNTHETIC CANNABINOL AND HOMOLOGS THEREOF

(71) Applicant: PURISYS LLC, Athens, GA (US)

(72) Inventors: Charla Barr, Monroe, GA (US); Achintya Sujan, Athens, GA (US); Wen-Chun Zhang, Bogart, GA (US); Akram M. Hazeen, Athens, GA (US); Joshua K. Hoerner, Watkinsville, GA (US)

(73) Assignee: PURISYS LLC, Athens, GA (US)

( * ) Notice: Subject to any disclaimer, the term of this patent is extended or adjusted under 35 U.S.C. 154(b) by 749 days.

(21) Appl. No.: 17/630,221

(22) PCT Filed: Jul. 24, 2020

(86) PCT No.: PCT/US2020/043507
§ 371 (c)(1),
(2) Date: Jan. 26, 2022

(87) PCT Pub. No.: WO2021/021632
PCT Pub. Date: Feb. 4, 2021

(65) Prior Publication Data
US 2022/0274942 A1 Sep. 1, 2022

Related U.S. Application Data

(60) Provisional application No. 62/879,089, filed on Jul. 26, 2019.

(51) Int. Cl.
*C07D 311/80* (2006.01)
(52) U.S. Cl.
CPC .................. *C07D 311/80* (2013.01)
(58) Field of Classification Search
CPC .................................................. C07D 311/80
See application file for complete search history.

(56) References Cited

PUBLICATIONS

Adams, R. et al., "Isolation of Cannabinol, Cannabidiol and Quebrachitol from Red Oil of Minnesota Wild Hemp," Journal of the American Chemical Society, 62:2194-2196, (Jan. 1, 1940).
Korte, F. et al., "Isolierung von haschisch-Inhaltsstoffen Aus Cannabis Sativa Non Indica," Justus Liebigs Annalen Der Chemie, Verlag Chemie GmbH, DE, 630:71-83, (Jan. 1, 1960).
Meltzer, P.C. et al., "An improved synthesis of cannabinol and cannabiorcol," Synthesis, 12:985-987, (Jan. 1, 1981).
Rhee, M.-H. et al., "Cannabinol Derivatives: Binding to Cannabinoid Receptors and Inhibition of Adenylylcyclase," Journal of Medicinal Chemistry, 40(20): 3228-3233, (Sep. 1, 1997).
WIPO Application No. PCT/US2020/043507, PCT International Preliminary Report on Patentability mailed Feb. 10, 2022, 11 pgs.
WIPO Application No. PCT/US2020/043507, International Search Report and Written Opinion of the International Searching Authority mailed Dec. 8, 2020, 18 pgs.

*Primary Examiner* — Golam M Shameem
(74) *Attorney, Agent, or Firm* — Alston & Bird LLP

(57) ABSTRACT

The present disclosure relates to the preparation of synthetic cannabinol and homologs thereof having the structure of Formula (I), wherein, n is 1, 2, 3 or 4. The methods described herein provide for high yields and purity in a one-pot synthesis or high yields and purity without the need for lengthy column chromatography. The present disclosure also relates to solid forms of cannabinol.

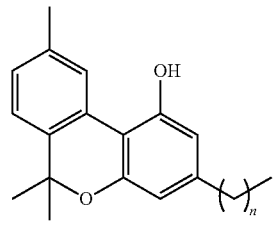

(I)

17 Claims, 19 Drawing Sheets

A.

B.

A.

B.

METHODS OF PREPARING SYNTHETIC CANNABINOL AND HOMOLOGS THEREOF

CROSS-REFERENCE TO RELATED APPLICATIONS

This application is a 35 U.S.C. § 371 national stage of International Application No. PCT/US2020/043507, filed Jul. 24, 2020, which claims priority to and the benefit of U.S. Provisional Application No. 62/879,089 filed Jul. 26, 2019, the contents of which are incorporated by reference in their entirety for all purposes.

FIELD

The subject matter described herein relates to methods for preparing synthetic cannabinol its alkyl homologs and compositions thereof.

BACKGROUND

Cannabinoids make up a class of diverse chemical compounds that act on cannabinoid receptors in the brain. Ligands for these receptor proteins include the endocannabinoids produced naturally in the body by animals. Plants also produce cannabinoids, sometimes referred to as phytocannabinoids. Over 100 different cannabinoids have been isolated from *cannabis*.

Cannabinol (CBN) is a mildly psychoactive cannabinoid found only in trace amounts in *cannabis*. In comparison, the most notable cannabinoid found in *cannabis* is tetrahydrocannabinol (THC), the primary psychoactive compound in *cannabis*. It has been reported that stored, degraded or oxidized *cannabis* products, such as low-quality baled *cannabis* and traditionally produced hashish, are higher in CBN. By way of example, when *cannabis* is exposed to air or ultraviolet light (for example, in sunlight) for a prolonged period, tetrahydrocannabinolic acid (THCA) can convert to cannabinolic acid (CBNA). CBN is then formed by decarboxylation of CBNA. CBN is also formed as a metabolite of THC.

CBN acts as a partial agonist at the CB1 receptors but has a higher affinity to CB2 receptors. Relative to THC, CBN has lower affinities for each receptor, about 7- to 8-fold lower for CB1 receptor and about 3-fold lower for CB2 receptor.

The preparation of CBN is complex. The preparation of CBN from plants involves separation from the plant by extraction with organic solvents. Hydrocarbons and alcohols are often used as solvents. However, these solvents are flammable, and many are toxic. Supercritical solvent extraction with carbon dioxide is an alternative technique. Once extracted, isolated components can be separated using wiped film vacuum distillation or other distillation techniques. Methods for preparing synthetic CBN are known. However, the synthetic routes require many steps, and involve column chromatography to isolate product of sufficient purity. In each of the above methods, the cost and the environmental impact of preparing CBN is burdensome.

What is therefore needed is are new synthetic methods to prepare CBN, that is a one-pot synthesis or does not also require chromatographic purification. The subject matter disclosed herein addresses these shortcomings of the art.

BRIEF SUMMARY

In certain aspects, the subject matter described herein is directed to a method of preparing a compound of Formula I,

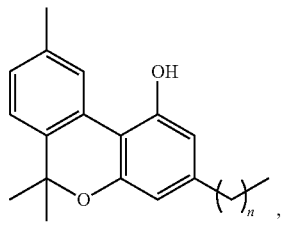

wherein, n is 1, 2, 3 or 4;
comprising,
contacting a compound of Formula II,

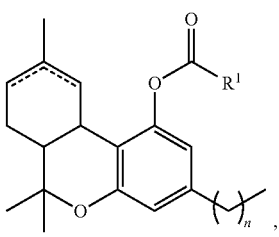

wherein,
n is 1, 2, 3 or 4; and
$R^1$ is an alkyl or aryl;
one of ===== is a double bond, the other is a single bond;
with an oxidant, optionally in the presence of a first solvent, to prepare a compound of Formula III,

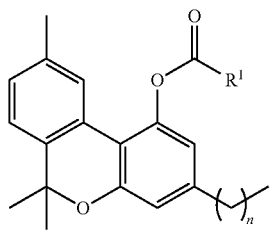

wherein,
n is 1, 2, 3 or 4; and
$R^1$ is an alkyl or aryl;
and,
contacting the compound of Formula III with a base in the presence of a second solvent to prepare a composition comprising a compound of Formula I.

In certain aspects, the subject matter described herein is directed to a method of preparing a compound of Formula I,

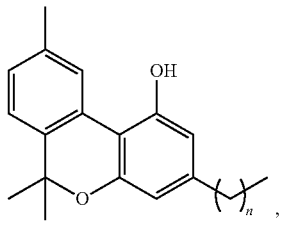

I wherein, n is 1, 2, 3 or 4;
comprising,
contacting a compound of Formula II,

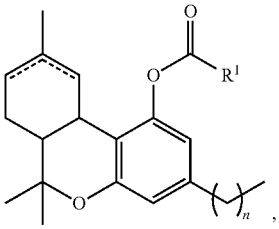

II wherein,
n is 1, 2, 3 or 4; and
R¹ is an alkyl or aryl;
one of ===== is a double bond, the other is a single bond;
with iodine in the presence of a first solvent to prepare a compound of Formula II,

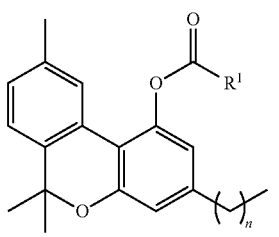

III wherein,
n is 1, 2, 3 or 4; and
R¹ is an alkyl or aryl;
crystallizing a compound of Formula III from at least two crystallizing solvents;
and,
contacting the compound of Formula III with a base in the presence of a second solvent to prepare a composition comprising a compound of Formula I.

In certain aspects, the subject matter described herein is directed to a method of preparing a compound of Formula I,

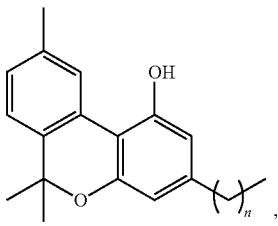

I wherein, n is 1, 2, 3 or 4;
comprising,
contacting a compound of Formula II,

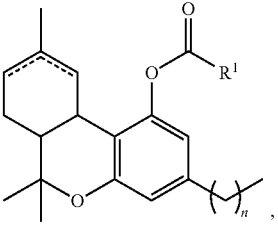

II wherein,
n is 1, 2, 3 or 4; and
R¹ is an alkyl or aryl;
one of ===== is a double bond, the other is a single bond;
with sulfur to prepare a compound of Formula III,

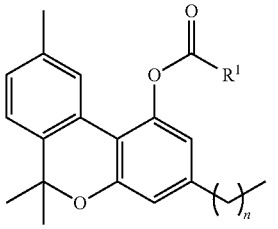

III wherein,
n is 1, 2, 3 or 4; and
R¹ is an alkyl or aryl;
contacting the compound of Formula III with a base in the presence of a second solvent to prepare a composition comprising a compound of Formula I;
and,
subjecting the composition to a fractional distillation to prepare a compound of Formula I.

In certain aspects, the methods above are directed to preparing a compound of Formula I, which is cannabinol.

In certain aspects, the subject matter described herein is directed to compositions comprising a compound of Formula I.

These and other aspects are described fully herein.

DETAILED DESCRIPTION

Disclosed herein are novel synthetic routes for the preparation of compounds of Formula I, such as cannabinol and 3-position alkyl homologs of cannabinol. The compounds are of the general Formula I:

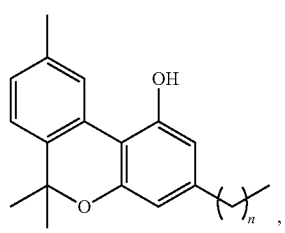

where, n is 1, 2, 3 or 4. In certain embodiments, the cannabinoid is cannabinol, having the structure:

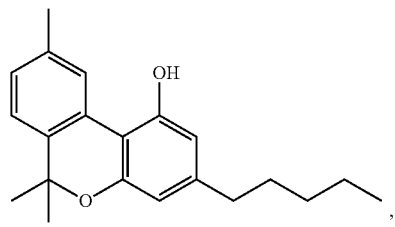

These compounds of Formula I are useful cannabinoids but are not readily obtainable by synthetic methods in significant quantity and/or purity. As described herein, the present methods allow for: preparation of highly pure compounds of Formula I, such as cannabinol or its alkyl homologs, without the need for column chromatography; or one-pot synthetic routes to prepare highly pure compounds of Formula I, such as cannabinol or its alkyl homologs. It has been found that the 1-position ester analogs, which are compounds of Formula III, can be recrystallized in suitable solvents. This, in part, provides exceptionally pure products, which are compounds of Formula I, without the need for column chromatography of the final product. Avoidance of column chromatography reduces costs and environmental impact. It has been found that a one-pot synthetic route can be utilized to prepare compounds of Formula I, such as cannabinol or its alkyl homologs. In this method, it was surprisingly found that the reaction is exceptionally clean, can be performed neat (in the absence of solvent), which does not require solvent, avoids the requirement to remove reagents, avoids the requirement to separate an intermediate as a solid, and proceeds in one-pot. In certain exemplified embodiments, the reaction can include, but is not required, contacting the reaction product mixture with an adsorbent to remove color, etc., but is not intended to separate compounds. In certain embodiments, the reaction can b is simply allowed to cool before hydrolysis. This method can include a fractional distillation to prepare exceptionally pure compounds of Formula I. Additionally, without the need for extensive purification, the yield represents the amount of final product. The present methods prepare the desired compounds in significant overall yields of about 40 to about 75%, for example 40-45%, 46%-50%; 51-55%, 56-60%, 61-65%, 66-70%, 71-75%.

Figure 15:
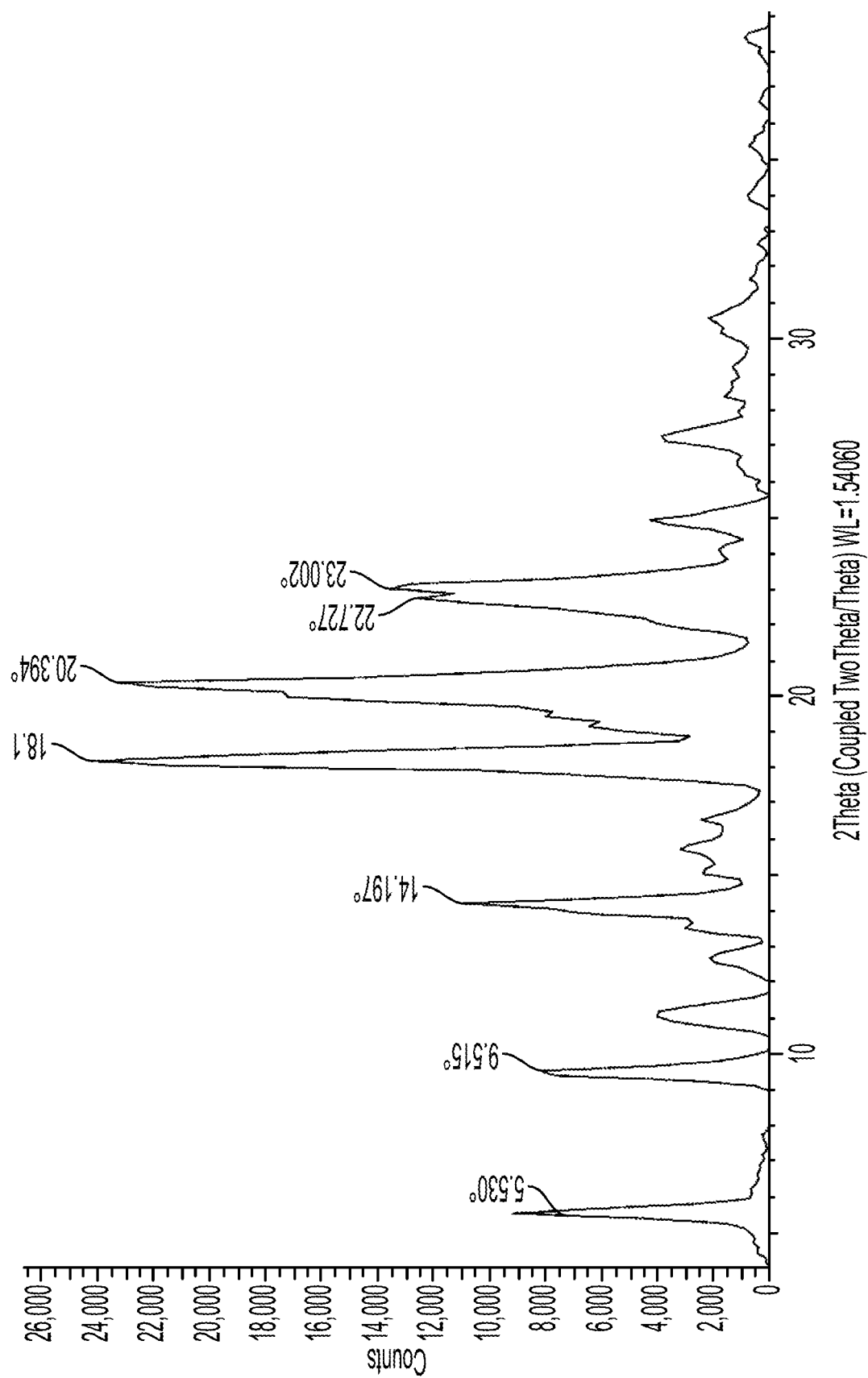
FIG. 15 shows a PXRD pattern of crystalline CNB prepared by a method described herein.
Figure 16:
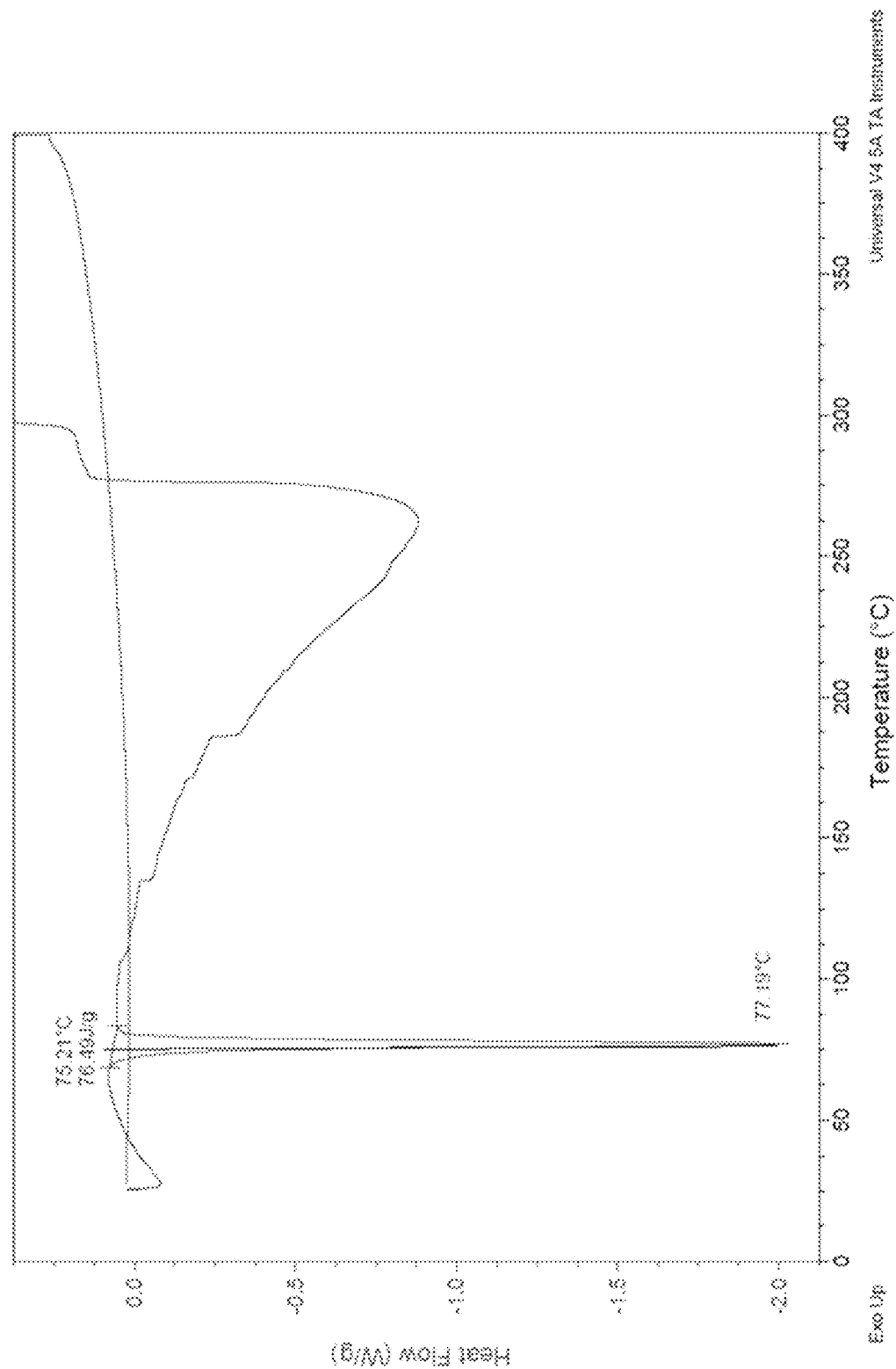
FIG. 16 shows a DSC thermogram for crystalline CBN prepared by a method described herein. The onset of m.p. of crystallized CBN solids was determined to be approximately 75° C., with a complete sharp m.p. that occurred at 77.2° C. as shown by DSC measurements.
Figure 17:
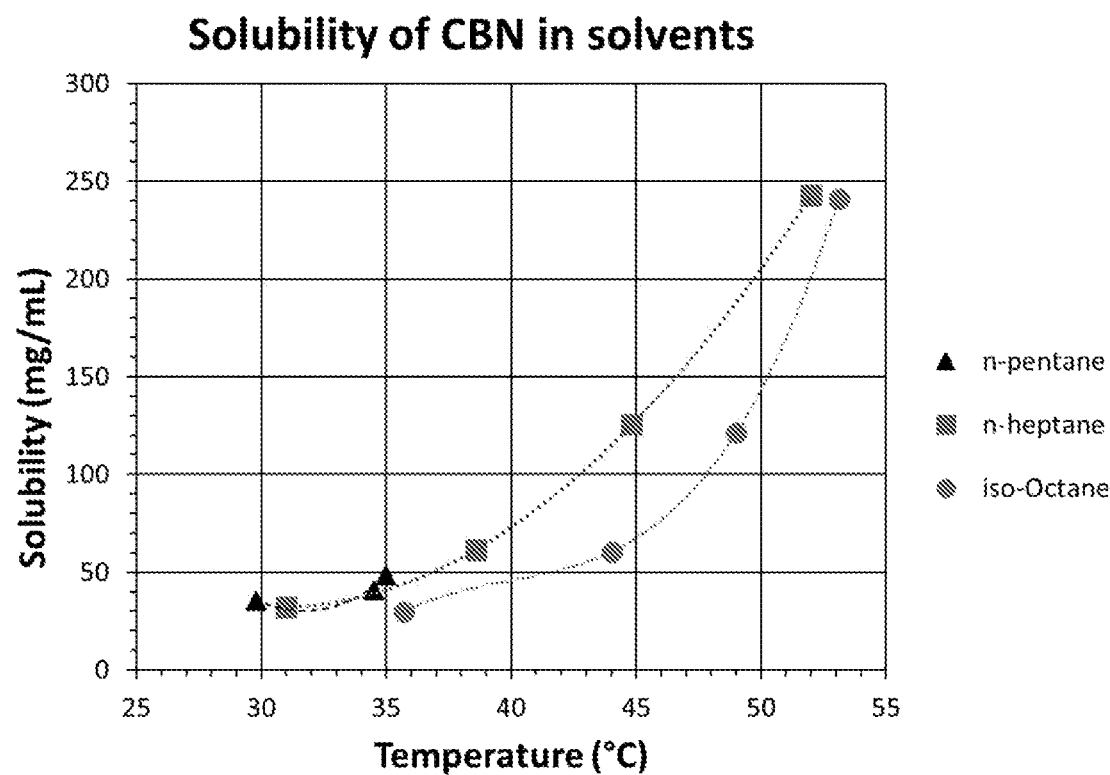
FIG. 17 reports on the solubility of CBN in certain solvents as determined in a screening protocol.

The preparation of CBN as described herein is advantageous over other synthetic methods which require many steps and involve lengthy column chromatography to isolate product of sufficient purity. Described herein, among other things, is the synthesis of CBN-NE (Formula III) that is of sufficient purity to avoid column chromatography in a one-pot synthesis. In embodiments, CBN oil is produced in >97% purity following the oxidation and subsequent hydrolysis step without the need for column chromatography. The CBN-NE intermediate (Formula III) produced in the oxidation step may be isolated and recrystallized to further increase the purity prior to the hydrolysis step. To further increase yield, the CBN-NE may also be purified through a silica pad or plug instead of recrystallization. A result of purifying the compounds of Formula III is the overall reaction proceeds to prepare compounds of Formula I at high yield and purity without the need for column chromatography. In embodiments, the CBN oil of Formula I is fractionally distilled to remove low level impurities and residual solvents to achieve purity >99%. The purified CBN oil may be crystallized by multiple heat and cooling cycles at temperatures between −20° C. to 60° C. The high purity of the CBN oil resulting from high purity CBN-NE is necessary for crystallization of the oil to occur. PXRD patterns of crystalline CBN prepared by the new methods is shown in FIG. 15.

Synthetic preparation of CBN by modified Ullmann-Ziegler cross-coupling is known. (Nüllen, M., and Göttlich, R., Synlett, 2013, 24, 1109-1112). This reference teaches that oxidation routes provide poor yields. (Id., p. 1109). Oxidation of tetrahydrocannabinol (THC) and cannabidiol (CBD) are known. Sulfur dehydrogenation of 9-Carbomethoxy-$D^8$-THC-3-(1',1-dimethylheptyl) is reported to proceed at 69% yield. (Mahadevan, A., et al., J. Med. Chem., 2000, 43, 3778-3785). This sulfur method teaches flash chromatography of the crude product. (Id., pp. 3782-3783). It was also reported that when the 1-position oxygen was converted to the phosphate derivative, the reaction resulted in undesirable ring-opening. (Id., pp. 3779-3780). Similarly, it has been reported that sulfur dehydrogenation of THC and CBD obtained from *cannabis* extract is followed by chromatography on a silica gel column. (Rhee, M-H., et al., J. Med. Chem., 1997, 40, 3228-3233). Oxidation of THC and CBD using iodine has been reported. (Pollastro, F., et al., J. Nat. Prod., 2018, 81, 630-633). However, the 1-position was a hydroxyl. This iodine method teaches GCC of the crude product. (Id., p. 632). The reported yield for conversion of THC is 70%, while CBD is 72% (Id., p. 631) for his specific step, with even lower reported overall yields. In addition to these art reactions failing to describe the compounds utilized in the present methodologies, the art methods do not describe clean reactions that proceed without significant purification, such as product separation, column chromatography, and the like, nor does the art suggest a one-pot synthetic methodology.

A particular compound of Formula I is cannabinol. Cannabinol is a cannabinoid found in the *Cannabis* plant. It is a metabolite of THC, with potential immunosuppressive and anti-inflammatory activities. Cannabinol preferentially binds to the cannabinoid G-protein coupled receptor CB2, which is mainly expressed on a variety of immune cells, such as T-cells, B-cells, macrophages and dendritic cells. Stimulation of CB2 receptors by cannabinol may both trigger apoptosis in these cells and inhibit the production of a variety of cytokines. Cannabinol exerts minimal affinity for CB1 and has a weak effect on the central nervous system. Producing synthetic cannabinol in commercially-viable quantities has been challenging. Described below are methods of preparing synthetic cannabinol and its alkyl analogs in yields and purity that are commercially scalable.

The potential therapeutic value of CBN in the treatment of diseases has stimulated research and development in formulating CBN for use in pharmaceutical compositions. Crystalline CBN could be more advantageous in one or more respects compared to other compositions of matter comprising CBN, including amorphous CBN, for example, in terms of chemical and physical stability, storage, processing, compatibility, and hygroscopicity. It is also possible that the crystalline composition could offer easier, quicker, and more extensive dissolution into solvents and more rapidly bioavailability when compared to other forms of CBN. Disclosed herein are unique synthetic routes for obtaining the desired CBN products, which can include crystalline CBN compositions.

The presently disclosed subject matter will now be described more fully hereinafter. However, many modifications and other embodiments of the presently disclosed subject matter set forth herein will come to mind to one skilled in the art to which the presently disclosed subject matter pertains having the benefit of the teachings presented in the foregoing descriptions. Therefore, it is to be understood that the presently disclosed subject matter is not to be limited to the specific embodiments disclosed and that modifications and other embodiments are intended to be included within the scope of the appended claims. In other words, the subject matter described herein covers all alternatives, modifications, and equivalents. In the event that one or more of the incorporated literature, patents, and similar materials differs from or contradicts this application, including but not limited to defined terms, term usage, described techniques, or the like, this application controls. Unless otherwise defined, all technical and scientific terms used herein have the same meaning as commonly understood by one of ordinary skill in this field. All publications, patent applications, patents, and other references mentioned herein are incorporated by reference in their entirety.

I. Definitions

As used herein, the "CBN" refers to cannabinol, "CBD" refers to cannabidiol and "THC" refers to tetrahydrocannabinol. As used herein, a "homolog" refers to any number of carbons in the chain at the 3-position of the core of Formula I.

The term "alkyl" as used herein refers to a saturated linear or branched-chain monovalent hydrocarbon radical of one to twelve carbon atoms ($C_1$-$C_{12}$), wherein the alkyl radical may be optionally substituted independently with one or more substituents. In another embodiment, an alkyl radical is one to eight carbon atoms ($C_1$-$C_8$), or one to six carbon atoms ($C_1$-$C_6$). Examples of alkyl groups include, but are not limited to, methyl (Me, —$CH_3$), ethyl (Et, —$CH_2CH_3$), 1-propyl (n-Pr, n-propyl, —$CH_2CH_2CH_3$), 2-propyl (i-Pr, i-propyl, —$CH(CH_3)_2$), 1-butyl (n-Bu, n-butyl, —$CH_2CH_2CH_2CH_3$), 2-methyl-1-propyl (i-Bu, i-butyl, —$CH_2CH(CH_3)_2$), 2-butyl (s-Bu, s-butyl, —$CH(CH_3)CH_2CH_3$), 2-methyl-2-propyl (t-Bu, t-butyl, —$C(CH_3)_3$), 1-pentyl (n-pentyl, —$CH_2CH_2CH_2CH_2CH_3$), 2-pentyl (—$CH(CH_3)CH_2CH_2CH_3$), 3-pentyl (—$CH(CH_2CH_3)_2$), 2-methyl-2-butyl (—$C(CH_3)_2CH_2CH_3$), 3-methyl-2-butyl (—$CH(CH_3)CH(CH_3)_2$), 3-methyl-1-butyl (—$CH_2CH_2CH(CH_3)_2$), 2-methyl-1-butyl (—$CH_2CH(CH_3)CH_2CH_3$), 1-hexyl (—$CH_2CH_2CH_2CH_2CH_2CH_3$), 2-hexyl (—$CH(CH_3)CH_2CH_2CH_2CH_3$), 3-hexyl (—$CH(CH_2CH_3)(CH_2CH_2CH_3)$), 2-methyl-2-pentyl (—$C(CH_3)_2CH_2CH_2CH_3$), 3-methyl-2-pentyl (—$CH(CH_3)CH(CH_3)CH_2CH_3$), 4-methyl-2-pentyl (—$CH(CH_3)CH_2CH(CH_3)_2$), 3-methyl-3-pentyl (—$C(CH_3)(CH_2CH_3)_2$), 2-methyl-3-pentyl (—$CH(CH_2CH_3)CH(CH_3)_2$), 2,3-dimethyl-2-butyl (—$C(CH_3)_2CH(CH_3)_2$), 3,3-dimethyl-2-butyl (—$CH(CH_3)C(CH_3)_3$, 1-heptyl, 1-octyl, and the like.

The term "aryl" as used herein means a monovalent aromatic hydrocarbon radical of 6-20 carbon atoms ($C_6$-$C_{20}$) derived by the removal of one hydrogen atom from a single carbon atom of a parent aromatic ring system. Aryl includes bicyclic radicals comprising an aromatic ring fused to a saturated, partially unsaturated ring, or aromatic carbocyclic ring. Typical aryl groups include, but are not limited to, radicals derived from benzene (phenyl), substituted benzenes, naphthalene, anthracene, biphenyl, indenyl, indanyl, 1,2-dihydronaphthalene, 1,2,3,4-tetrahydronaphthyl, and the like. In certain embodiments, the aryl group contains 6-10 carbons ($C_6$-$C_{10}$). Aryl groups are optionally substituted independently with one or more substituents.

As used herein, the term "contacting" refers to allowing two or more reagents to contact each other. The contact may or may not be facilitated by mixing, agitating, stirring, and the like.

The term "column chromatography" or "lengthy column chromatography" refers to purification using standard length columns as would be understood by those of skill in the art. Column chromatography is known to refer to the separation of bulk substances based on differential adsorption of compounds to the adsorbent in a column, where compounds move through the column at different rates, which allows different compounds to be separated into fractions. Short filtration, such as a silica pad or plug, is not included in this meaning.

As used herein, the term "oxidant" refers to an agent having the ability to remove one or more electrons from a molecule.

As used herein, "API" refers to Active Pharmaceutical Agent.

As used herein, "substantially free" refers to trace amounts or levels of about 1% w/w or less. As used herein, "essentially free" refers to levels that are below trace. In certain embodiments, essentially free refers to amounts not detectable by standard techniques.

As used herein, the term "crystalline" and related terms used, when used to describe a substance, component, product, or form, mean that the substance, component, product, or form is substantially crystalline, for example, as determined by X-ray diffraction. (see, e.g., *Remington's Pharmaceutical Sciences*, 20$^{th}$ ed., Lippincott Williams & Wilkins, Philadelphia Pa., 173 (2000); *The United States Pharmacopeia*, 37$^{th}$ ed., 503-509 (2014)). The crystallization and recrystallization described herein can produce crystalline materials.

As used herein, and unless otherwise specified, a solid form that is "substantially chemically pure" is substantially free from other chemical compounds (i.e., chemical impurities). In certain embodiments, a solid form that is substantially chemically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other chemical compounds on a weight basis. The detection of other chemical compounds can be accomplished by any method apparent to a person of ordinary skill in the art, including, but not limited to, methods of chemical analysis, such as, e.g., mass spectrometry analysis, spectroscopic analysis, thermal analysis, elemental combustion analysis and/or chromatographic analysis.

As used herein, and unless otherwise indicated, a chemical compound, solid form, or composition that is "substantially free" of another chemical compound, solid form, or composition means that the compound, solid form, or composition contains, in certain embodiments, less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2% 0.1%, 0.05%, or 0.01% by weight of the other compound, solid form, or composition.

Unless otherwise specified, the term "composition" as used herein is intended to encompass a product comprising the specified ingredient(s) (and in the specified amount(s), if indicated), as well as any product which results, directly or indirectly, from combination of the specified ingredient(s) in the specified amount(s). Additionally, the term "composition" refers to a mixture of compounds.

Unless otherwise specified, the term "crystalline" and related terms used herein, when used to describe a substance, component, product, or form, mean that the substance, component, product, or form is substantially crystalline, for example, as determined by X-ray diffraction. (see, e.g., *Remington's Pharmaceutical Sciences*, 20$^{th}$ ed., Lippincott Williams & Wilkins, Philadelphia Pa., 173 (2000); *The United States Pharmacopeia*, 37$^{th}$ ed., 503-509 (2014)).

As used herein, the term "multiple heat and cooling cycles" refers to at least one cycle. In certain embodiments, the number of cycles is from 1 to 20, or more. In certain embodiments, the number of cycles is from 2 to 15, or 2, 3, 4, 5, 6, 7, 8, 9, 10, 11, 12, 13, 14, or 15 cycles.

By "pharmaceutically acceptable," it is meant a diluent, excipient, or carrier in a formulation must be compatible with the other ingredient(s) of the formulation and not deleterious to the recipient thereof.

Unless otherwise specified, to the extent that there is a discrepancy between a depicted chemical structure of a compound provided herein and a chemical name of a compound provided herein, the chemical structure shall control.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of a particular disease.

A "patient" or "individual" or "subject" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the patient, individual, or subject is a human.

As used herein, the term "therapeutic amount" refers to an amount of a therapeutic agent, compound, formulation, material, or composition, as described herein effective to achieve a particular biological result. Such results may include, but are not limited to, the inhibition of a disease as determined by any means suitable in the art.

As used herein, the term "pharmaceutically acceptable excipient" refers to an ingredient in a pharmaceutical formulation, other than an active ingredient, which is nontoxic to a subject. A pharmaceutically acceptable excipient includes, but is not limited to, a buffer, carrier, stabilizer, or preservative.

As used herein, and unless otherwise specified, the terms "about" and "approximately," when used in connection with a numeric value or range of values which is provided to characterize a particular solid form, e.g., a specific temperature or temperature range, such as, for example, that describes a melting, dehydration, desolvation, or glass transition temperature; a mass change, such as, for example, a mass change as a function of temperature or humidity; a solvent or water content, in terms of, for example, mass or a percentage; or a peak position, such as, for example, in analysis by, for example, IR or Raman spectroscopy or PXRD; indicate that the value or range of values may deviate to an extent deemed reasonable to one of ordinary skill in the art while still describing the solid form. Techniques for characterizing crystal forms and amorphous forms include, but are not limited to, thermal gravimetric analysis (TGA), differential scanning calorimetry (DSC), X-ray powder diffraction (PXRD), single-crystal X-ray diffraction, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility studies, and dissolution studies. In certain embodiments, the terms "about" and "approximately," when used in this context, indicate that the numeric value or range of values may vary within 30%, 20%, 15%, 10%, 9%, 8%, 7%, 6%, 5%, 4%, 3%, 2%, 1.5%, 1%, 0.5%, or 0.25% of the recited value or range of values. In the context of molar ratios, "about" and "approximately" indicate that the numeric value or range of values may vary within 20%, 15%, 10%, 9%, 8%, 7%, 6%, 5%, 4%, 3%, 2%, 1.5%, 1%, 0.5%, or 0.25% of the recited value or range of values. It should be understood that the numerical values of the peaks of an X-ray powder diffraction pattern may vary from one machine to another, or from one sample to another, and so the values quoted are not to be construed as absolute, but with an allowable variability, such as ±0.20 degrees two theta (° 2θ), or more. For example, in some embodiments, the value of an PXRD peak position may vary by up to ±0.20 degrees 2θ while still describing the particular PXRD peak.

As used herein, and unless otherwise specified, a solid form that is "substantially physically pure" is substantially free from other solid forms. In certain embodiments, a crystal form that is substantially physically pure contains less than about 50%, 45%, 40%, 35%, 30%, 25%, 20%, 15%, 10%, 9%, 8%, 7%, 6%, 5%, 4%, 3%, 2%, 1%, 0.5%, 0.4%, 0.3%, 0.2%, 0.1%, 0.05%, or 0.01% of one or more other solid forms on a weight basis. The detection of other solid forms can be accomplished by any method apparent to a person of ordinary skill in the art, including, but not limited to, diffraction analysis, thermal analysis, elemental combustion analysis and/or spectroscopic analysis.

Additional definitions are provided below.

II. Methods of Preparing Compounds of Formula I

In certain embodiments, the subject matter described herein is directed to methods of preparing a compound of Formula I,

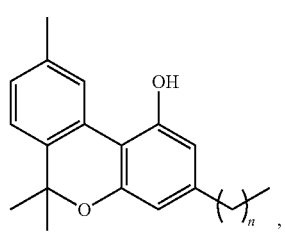

wherein, n is 1, 2, 3 or 4;

comprising,
contacting a compound of Formula II,

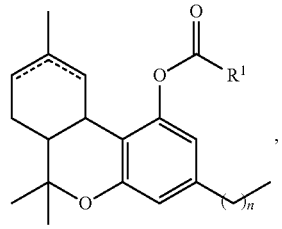

wherein,
n is 1, 2, 3 or 4; and
$R^1$ is an alkyl or aryl;
one of ===== is a double bond, the other is a single bond;
with an oxidant, optionally in the presence of a first solvent, to prepare a compound of Formula III,

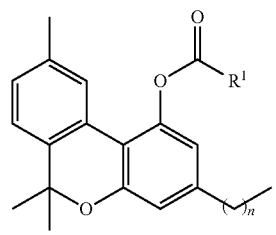

wherein,
n is 1, 2, 3 or 4; and
$R^1$ is an alkyl or aryl;
and,
contacting the compound of Formula III with a base in the presence of a second solvent to prepare a composition comprising a compound of Formula I.

In certain embodiments, n is 2 or 4. In certain embodiments, n is 4.

In certain embodiments, $R^1$ is an optionally substituted straight or branched $C_{1-12}$ alkyl or optionally substituted $C_{6-20}$ aryl. In certain embodiments, $R^1$ is an optionally substituted straight or branched $C_{1-6}$ alkyl or optionally substituted $C_{6-10}$ aryl. In certain embodiments, $R^1$ is methyl, ethyl, n-propyl, isopropyl, n-butyl, sec-butyl, t-butyl, isobutyl, pentyl, neopentyl, or hexyl. In certain embodiments, $R^1$ is a $C_{6-10}$ aryl selected from the group consisting of phenyl, indenyl and naphthalenyl. In certain embodiments, $R^1$ is naphthalenyl.

In certain embodiments, the contacting of a compound of Formula II with an oxidant is at a temperature, $T^1$, from about 100° C. to about 400° C. In certain embodiments, $T^1$ is from about 150° C. to about 350° C. In certain embodiments, $T^1$ is from about 200° C. to about 300° C. In certain embodiments, $T^1$ is from about 220° C. to about 270° C.

In certain embodiments, the contacting of a compound of Formula II with an oxidant is for a period of about 5 minutes to about 96 hours; or about 10 minutes to about 84 hours; or about 20 minutes to about 72 hours; or about 48 hours to about 72 hours; or about 30 minutes to about 6 hours; or about 45 minutes to about 2 hours.

In certain embodiments, the oxidant is $I_2$ or sulfur. In certain embodiments, the oxidant is $I_2$. In certain embodiments, the oxidant is sulfur. In certain embodiments, the oxidant is present in an amount of about 1 equivalent to about 5 equivalents. In certain embodiments, the oxidant is present in an amount of about 1.5 equivalent to about 4.5 equivalents. In certain embodiments, the oxidant is present in an amount of about 1.6, 1.7, 1.8, 1.9, 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, or 4.4 equivalents.

In certain embodiments, the optional first solvent is selected from the group consisting of toluene, acetone, methanol or other $C_{1-4}$ alcohol, 2-butanone, ethyl acetate, 1-4-dioxane, diethyl ether, tert-butyl methyl ether, tetrahydrofuran, dichloromethane, chloroform, heptane, isopropyl acetate, isooctane, n-decane, and anisole, and mixtures thereof. In certain embodiments, the first solvent is toluene. When the oxidant is sulfur, it is preferable that there is no first solvent.

In certain embodiments, the contacting of a compound of Formula III with a base is at a temperature, $T^2$, from about 0° C. to about 150° C. In certain embodiments, $T^2$ is from about 10° C. to about 130° C. In certain embodiments, $T^2$ is from about 20° C. to about 110° C. In certain embodiments, $T^2$ is from about 30° C. to about 50° C.

In certain embodiments, the contacting of a compound of Formula III with a base is for a period of about 5 minutes to about 12 hours; or about 10 minutes to about 6 hours; or about 20 minutes to about 3 hours; or about 30 minutes to about 2 hours; or about 45 minutes to about 1.5 hours.

In certain embodiments, the second solvent is selected from the group consisting of THF, methanol, methyl-THF, ethanol, isopropanol, butanol or other $C_{1-4}$ alcohol, DMF and water, and mixtures thereof.

In certain embodiments, the base is a metal hydroxide, for example, LiOH, KOH, NaOH, $Sr(OH)_2$, $Ba(OH)_2$, $Ca(OH)_2$, or RbOH. In certain embodiments, the base is an alkali metal hydroxide, which is comprised of an alkali metal cation and a hydroxide anion. In certain embodiments, the base is selected from the group consisting of LiOH, NaOH, KOH, RbOH, and CsOH. In certain embodiments, the base is LiOH. The base can be provided as an aqueous solution. In certain embodiments, the base is present in an amount from about 1 equivalent to about 10 equivalents, or from about 2 equivalents to about 4 equivalents, or about 2.0, 2.1, 2.2, 2.3, 2.4, 2.5, 2.6, 2.7, 2.8, 2.9, 3.0, 3.1, 3.2, 3.3, 3.4, 3.5, 3.6, 3.7, 3.8, 3.9, 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, 9.0, 9.1, 9.2, 9.3, 9.4, 9.5, 9.6, 9.7, 9.8, 9.9 or 10.0 equivalents.

In certain embodiments, it is advantageous that the reaction can prepare the compounds of Formula I without the need for column chromatography to purify a compound of Formula I or an intermediate thereof. As used herein, column chromatography refers to the separation of bulk substances based on differential adsorption of compounds to the adsorbent in a column, where compounds move through the column at different rates, which allows different compounds to be separated into fractions. In certain embodiments, the methods that do not comprise column chromatography are those where the oxidant is iodine.

It has been found that during performance of the methods, purifying a compound of Formula III by crystallization and re-crystallization provides excellent yield and purity of the desired products, which are compounds of Formula I. At least one advantage of the present methods over known methods is the high overall yield where the intermediate compounds of Formula III are solids or crystalline, easy to handle, and are obtained in high chemical purity by crystallization alone, without the need to perform any other purification method. Suitable crystallization and recrystallization methods include, but are not limited to, concentrating (e.g., by heating to remove solvent), cooling, precipitating with an antisolvent, seeding, and/or slurrying the solution. In certain embodiments, the methods comprise heating and cooling.

Optionally, the compounds of Formula III obtained in the crystallization step may be recrystallized to further increase purity. Recrystallization techniques are known in the art. Suitable crystallization and recrystallization solvents include, but are not limited to, ethyl acetate, methyl tert-butyl ether, n-propanol, methanol, isopropanol, ethanol, isopropyl acetate, n-propyl acetate, acetonitrile, n-butyl acetate, isobutyl methyl ketone, acetone, 2-butanone, water, and mixtures thereof. In certain embodiments, the crystallization solvent and the recrystallization solvent each is a mixture of at least two solvents from the list above. In certain embodiments, the mixture comprises acetone and methanol. The two solvents will be present in ratios of one to the other. The ratio can be any value from 0.01:1. In certain embodiments, the solvent mixture is acetone/methanol at a ratio of 0.1:1, or 0.2:1, or 0.3:1, or 0.4:1, or 0.5:1, or 0.6:1, or 0.7:1, or 0.8:1, or 0.9:1, or 1:1. Water may be used as an antisolvent to help precipitate the desired compounds. Exemplary crystallization and recrystallization methods are described elsewhere herein.

A result of purifying the compounds of Formula III is the overall reaction proceeds to prepare compounds of Formula I at high yield and purity without the need for column chromatography. In certain embodiments, the compound of Formula III has a purity (area %, also referred to as AUC) of at least 70%, 71%, 72%, 73%, 74%, 75%, 76%, 77%, 78%, 79% or 80% prior to proceeding to prepare a corresponding compound of Formula I. In certain embodiments, the compound of Formula III has a purity (AUC) of at least 90% prior to proceeding to prepare a corresponding compound of Formula I. In certain embodiments, the compound of Formula III has a purity (AUC) of at least 99% prior to proceeding to prepare a corresponding compound of Formula I. In certain embodiments, the compound of Formula III has a purity (AUC) of at least 99.1%, 99.2%, 99.3%, 99.4%, 99.5%, 99.6%, 99.7%, 99.8%, 99.9% or higher prior to proceeding to prepare a corresponding compound of Formula I.

In certain embodiments, the compound of Formula I prepared by the methods has a purity (AUC) of at least 90%. In certain embodiments, the compound of Formula I has a purity (AUC) of at least 99%, or about 99.1%, 99.2%, 99.3%, 99.4%, 99.5%, 99.6%, 99.7%, 99.8%, 99.9% or higher.

In certain embodiments, the oxidation of a compound of Formula II and the hydrolysis of a compound of Formula III can be performed in a one-pot reaction process. As used herein, the term "one-pot reaction" and the like refers to a reaction in which a starting material undergoes at least two sequential chemical transformations in a single reaction vessel. In general, compounds formed as intermediates in the sequence are not isolated from a one-pot reaction mixture. Reagents necessary to affect the transformation sequence may be added together at the beginning of the sequence, or they may be added one after another as the sequence progresses. In certain embodiments of the one-pot method, the oxidant is sulfur.

The one-pot method may further comprise a fractional distillation step to purify a compound of Formula I. The term "distillation" is intended to denote the type of separation conventional in chemical engineering and described, for example, in "Perry's Chemical Engineers' Handbook" in the 13th section of the 7th edition, and, is generally a method of separating mixtures based on differences in their volatilities in a boiling liquid mixture. The term "fractional distillation" is understood to mean a series of distillations where the distillate is withdrawn batch wise. Generally, a fractioning column is connected to a reflux condenser and a means for collecting fractions. Fractions can be collected at any desired temperature or range of temperatures. In certain embodiments, at least one fraction is collected from about 210° C. to about 219° C. In certain embodiments, at least one fraction is collected from about 2226° C. to about 230° C. In certain embodiments, at least one fraction is collected at a temperature of at least 245° C.

In certain embodiments, one or more distillates are combined. In certain embodiments, the compound of Formula I in the distillate has a purity (AUC) of at least 80%. In certain embodiments, the compound of Formula I in the distillate has a purity (AUC) of at least 90%. In certain embodiments, the compound of Formula I in the distillate has a purity (AUC) of at least 99%, or about 99.1%, 99.2%, 99.3%, 99.4%, 99.5%, 99.6%, 99.7%, 99.8%, 99.9% or higher.

A highly pure CBN crystal can be obtained by recrystallization. A method of recrystallizing CBN comprises dispersing CBN solids in 1-10 volumes of a high MW non-polar, branched hydrocarbon solvent at about room temperature to form a mixture; heating the mixture to about 70° C. to dissolve the CBN solids to form a solution; Cooling the solution to about 40° C.; Seeding the said solution at about 40° C. with a CBN seed (1 wt %) to prepare a suspension; Allowing the suspension to warm to about 40° C. with stirring; Allowing the suspension to stir at about 40° C. for at least 60 min; Cooling the suspension to about 10° C. over about 120 min; Separating the solid material via filtration from the suspension; Washing the solid material with about 2 volumes iso-octane at about −20° C.; and Drying the solid material at about 40° C. under vacuum for at least 12 h to obtain a crystalline CBN (65.4 g, 96.6% yield).

In certain embodiments, the CBN is in crystalline form. Compositions described herein can also comprise a crystalline form of CBN. A crystalline form of CBN can be prepared as described elsewhere herein. In certain embodiments, the crystalline CBN is formed by heat and cooling cycles of a pure amorphous CBN as prepared by methods described herein. Inn certain embodiments, the crystalline CBN is formed by seeding a pure amorphous CBN as prepared by methods described herein. In certain embodiments, the crystalline CBN is formed by heat and cooling cycles of an amorphous CBN, wherein the amorphous CBN is heated in a high MW (high MW refers to higher than pentane) non-polar solvent and cooled. In certain embodiments, the solvent is a high MW non-polar branched solvent, for example, iso-octane. It has been found that using such a high MW non-polar, branched solvent, iso-octane, in particular, results in a high yield of at least 95% using a reasonable quantity of solvent to fully dissolve the CBN. Compared to pentane, iso-octane provides greater dissolution with a reduced quantity of solvent. N-heptane was also shown to work. However, n-heptane results in a lower yield (presumably due to increased loss to mother liquor). In certain embodiments, the loss is less than 5% wt., 4% wt., 3% wt., 2% wt., or 1.5% wt. Iso-octane was used to crystallize CBN and generate the PXRD and PSD data. The experiments indicate that a high MW branched, non-polar solvent provides better a manufacturing option to achieve high yield and throughput.

Crystalline CBN can have desired particle sizes, as determined by known standard procedures. In certain embodiments, a crystalline cannabinol can have particle size: D10 of about 30 μm, 26 μm, or 20 μm. In certain embodiments, a crystalline cannabinol can have particle size: D50 of about 350 μm, 337 μm, or 300 μm. In certain embodiments, a crystalline cannabinol can have particle size: D90 of about 1500 μm, 1330 μm, or 1000 μm. In certain embodiments, a crystalline cannabinol can have particle size: D10 of about 30 μm, 26 μm, or 20 μm. In certain embodiments, a crystalline cannabinol can have particle size: D50 of about 40 μm, 56 μm, or 80 μm. In certain embodiments, a crystalline cannabinol can have particle size: D90 of about 100 μm, 156 μm, or 200 μm.

It will be understood that values of the variables in the starting materials of Formula II and intermediates of Formula III will be in accord with those respective variables in the final products of Formula I.

General Procedures

Compounds of Formula I and intermediates of Formulae II and III can be synthesized by synthetic routes described herein. Starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, Reagents for Organic Synthesis, v. 1-23, Wiley, N.Y. (1967-2006 ed.), or Beilsteins Handbuch der organischen Chemie, 4, Aufl. ed. Springer-Verlag, Berlin, including supplements (also available via the Beilstein online database).

Those of skill in this art are aware of synthetic chemistry transformations and protecting group methodologies (protection and deprotection) that in combination with the reactions disclosed herein are useful in synthesizing Formula I compounds (and any intermediates) and necessary reagents and intermediates are known in the art and include, for example, those described in R. Larock, Comprehensive Organic Transformations, VCH Publishers (1989); T. W. Greene and P. G. M. Wuts, Protective Groups in Organic Synthesis, 3rd Ed., John Wiley and Sons (1999); and L. Paquette, ed., Encyclopedia of Reagents for Organic Synthesis, John Wiley and Sons (1995) and subsequent editions thereof.

In preparing compounds of Formulas I, protection of functionality (e.g., alcohols) of intermediates may be necessary. The need for such protection will vary depending on the nature of the remote functionality and the conditions of the preparation methods. The need for such protection is readily determined by one skilled in the art. For a general description of protecting groups and their use, see T. W. Greene, Protective Groups in Organic Synthesis, John Wiley & Sons, New York, 1991.

Scheme 1 is a general synthetic route for preparing a compound of Formula I.
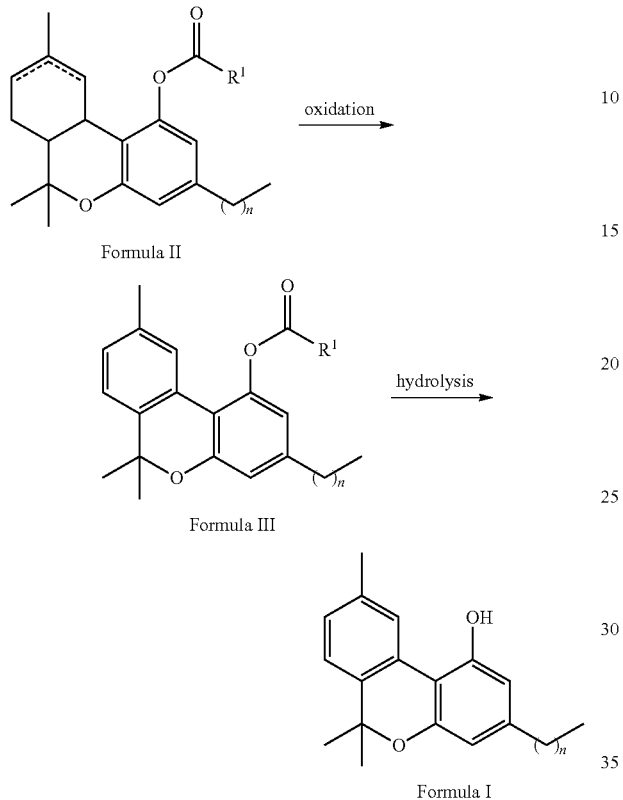
In certain embodiments, the methods are directed to synthetic routes for preparing cannabinol, such as the route described in Scheme 2.
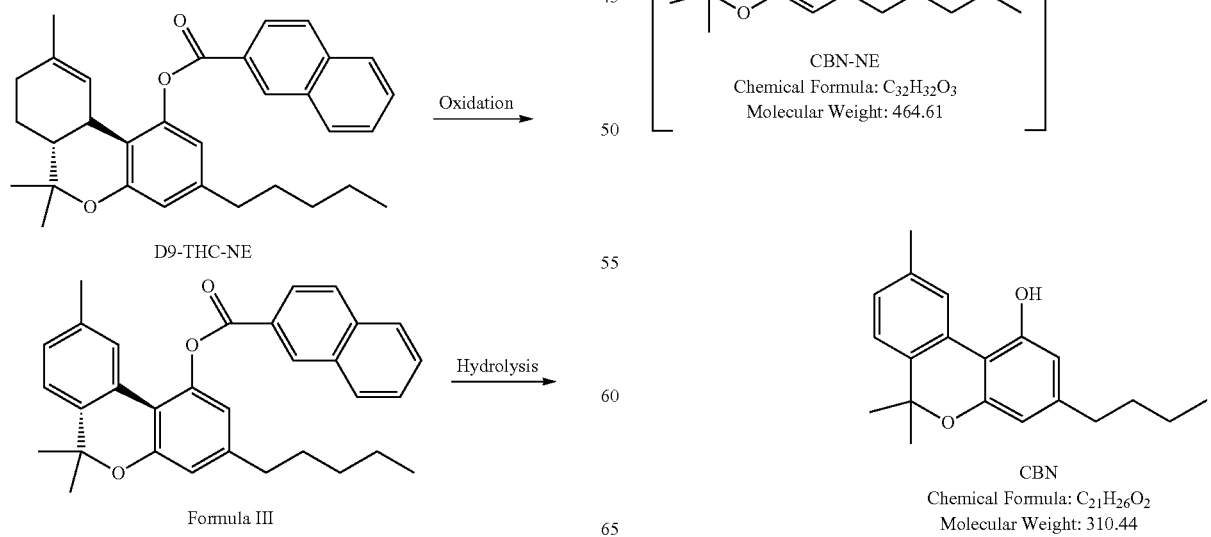
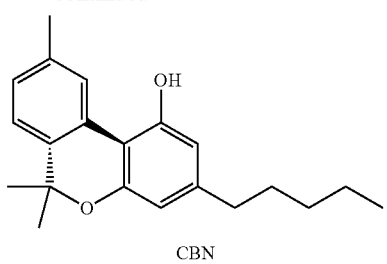
In certain embodiments, the synthetic route may further comprise the synthesis of D9-THC-NE, such as the route depicted in Schemes 3 and 4.
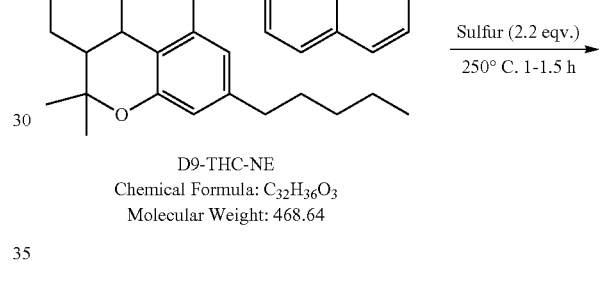

Scheme 4.

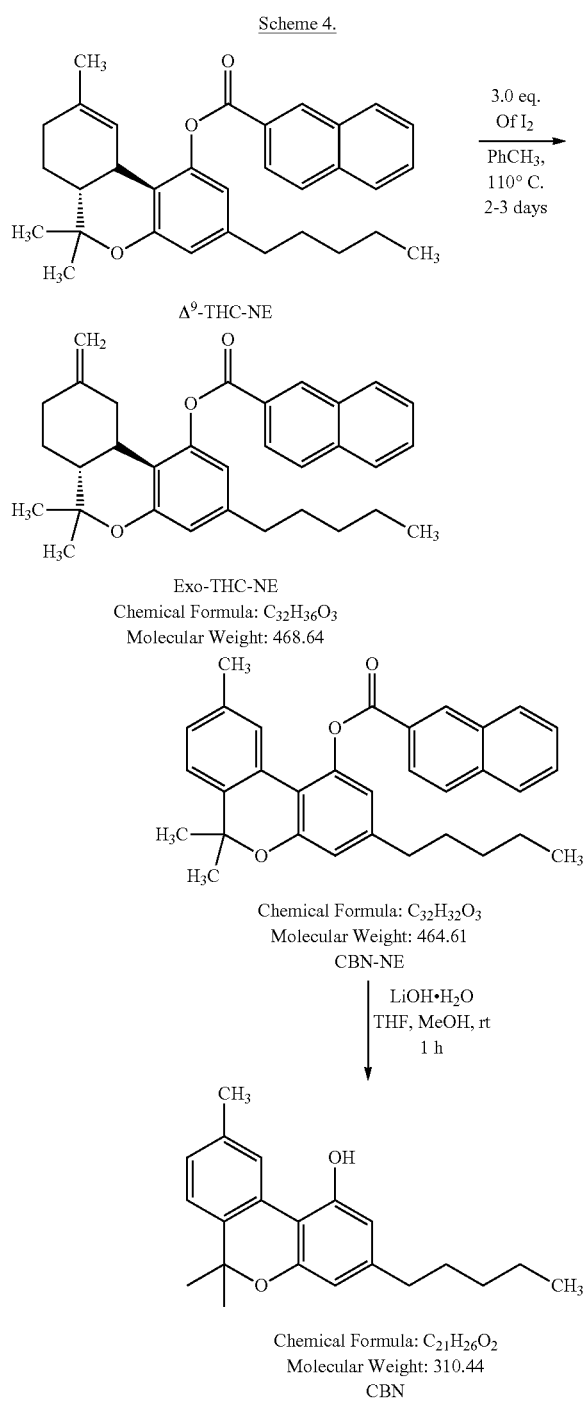

In the schemes above, the compound of Formula III, for example D8-THC-NE and D9-THC-NC, is re-crystallized as described elsewhere herein. The yields and purity of the final product are unexpectedly higher than art methods.

In certain embodiments, the methods further comprise quenching of the reaction mixture, whereby the reaction mixture is separated into a top organic layer and a bottom aqueous layer. In embodiments, the organic layer is extracted. In certain embodiments, the organic layer is washed with water.

In certain embodiments, the methods further comprise use of an iodine trap to collect iodine fumes.

The General Procedures and Examples provide exemplary methods for preparing Formula I compounds. Those skilled in the art will appreciate that routine modifications to the synthetic routes may be used to synthesize the Formula I compounds. Although specific starting materials and reagents are depicted and discussed in the schemes, General Procedures, and Examples, other starting materials and reagents may be substituted to provide a variety of derivatives and/or reaction conditions.

III. Indications and Methods of Treatment

It is contemplated that the compounds of Formula I disclosed herein may be used as analgesics, antibiotics, and/or to treat a disease responsive to immunosuppressive and anti-inflammatory properties of CBN or responsive to CBN's affinity to cannabinoid receptors. The diseases may include, but are not limited to, emesis, pain, epilepsy, Alzheimer's disease, Huntington's disease, Tourette's syndrome, glaucoma, osteoporosis, schizophrenia, cancer, obesity, autoimmune diseases, diabetic complications, infections against methicillin-resistant *Staphylococcus aureus*, nausea, depression, anxiety, Hypoxia-ischemia injuries, psychosis, and inflammatory diseases.

Autoimmune diseases include, for example, Acquired Immunodeficiency Syndrome (AIDS), alopecia areata, ankylosing spondylitis, antiphospholipid syndrome, autoimmune Addison's disease, autoimmune hemolytic anemia, autoimmune hepatitis, autoimmune inner ear disease (AIED), autoimmune lymphoproliferative syndrome (ALPS), autoimmune thrombocytopenia purpura (ATP), Behcet's disease, cardiomyopathy, celiac sprue-dermatitis hepetiformis; chronic fatigue immune dysfunction syndrome (CFIDS), chronic inflammatory demyelinating polyneuropathy (CIPD), cicatricial pemphigold, cold agglutinin disease, crest syndrome, Crohn's disease, Degos' disease, dermatomyositis-juvenile, discoid lupus, essential mixed cryoglobulinemia, fibromyalgia-fibromyositis, Graves' disease, Guillain-Barre syndrome, Hashimoto's thyroiditis, idiopathic pulmonary fibrosis, idiopathic thrombocytopenia purpura (ITP), IgA nephropathy, insulin-dependent diabetes mellitus, juvenile chronic arthritis (Still's disease), juvenile rheumatoid arthritis, Meniere's disease, mixed connective tissue disease, multiple sclerosis, myasthenia gravis, Parkinson's disease, pernacious anemia, polyarteritis nodosa, polychondritis, polyglandular syndromes, polymyalgia rheumatica, polymyositis and dermatomyositis, primary agammaglobulinemia, primary biliary cirrhosis, psoriasis, psoriatic arthritis, Raynaud's phenomena, Reiter's syndrome, rheumatic fever, rheumatoid arthritis, sarcoidosis, scleroderma (progressive systemic sclerosis (PSS), also known as systemic sclerosis (SS)), Sjögren's syndrome, stiff-man syndrome, systemic lupus erythematosus, Takayasu arteritis, temporal arteritis/giant cell arteritis, ulcerative colitis, uveitis, vitiligo and Wegener's granulomatosis.

Inflammatory disorders, include, for example, chronic and acute inflammatory disorders. Examples of inflammatory disorders include Alzheimer's disease, asthma, atopic allergy, allergy, atherosclerosis, bronchial asthma, eczema, glomerulonephritis, graft vs. host disease, hemolytic anemias, osteoarthritis, inflammatory bowel disease, sepsis, stroke, transplantation of tissue and organs, vasculitis, diabetic retinopathy and ventilator induced lung injury.

Examples of cancer to be treated herein include, but are not limited to, carcinoma, lymphoma, blastoma, sarcoma, and leukemia or lymphoid malignancies. More particular examples of such cancers include squamous cell cancer (e.g. epithelial squamous cell cancer), lung cancer including small-cell lung cancer, non-small cell lung cancer, adenocarcinoma of the lung and squamous carcinoma of the lung, cancer of the peritoneum, hepatocellular cancer, gastric or stomach cancer including gastrointestinal cancer, pancreatic cancer, glioblastoma, cervical cancer, ovarian cancer, liver cancer, bladder cancer, hepatoma, breast cancer, colon cancer, rectal cancer, colorectal cancer, endometrial or uterine carcinoma, salivary gland carcinoma, kidney or renal cancer, prostate cancer, vulval cancer, thyroid cancer, hepatic carcinoma, anal carcinoma, penile carcinoma, as well as head and neck cancer.

The CBN may be administered by any route appropriate to the condition to be treated, including orally, intravenously, topically, as well as by ophthalmic (eye drops), and transdermal (skin patch) modes.

The CBN can be used either alone or in combination with other agents in a therapy. For instance, the CBN compositions may be co-administered with at least one additional therapeutic agent. Such combination therapies noted above encompass combined administration (where two or more therapeutic agents are included in the same or separate formulations), and separate administration, in which case, administration of the CBN composition can occur prior to, simultaneously, and/or following, administration of the additional therapeutic agent and/or adjuvant.

IV. Formulations

Pharmaceutical formulations where the API is CBN as prepared by the methods described herein can be formulated for various routes of administration. CBN having the desired degree of purity is optionally mixed with one or more pharmaceutically acceptable excipients (Remington's Pharmaceutical Sciences (1980) 16th edition, Osol, A. Ed.). CBN can be formulated in accordance with standard pharmaceutical practice as a pharmaceutical composition. In embodiments, a CBN formulation comprises cannabinol and a pharmaceutically acceptable excipient.

A typical formulation is prepared by mixing CBN with excipients, such as carriers and/or diluents. Suitable carriers, diluents and other excipients are well known to those skilled in the art and include materials such as carbohydrates, waxes, water soluble and/or swellable polymers, hydrophilic or hydrophobic materials, gelatin, oils, solvents, water and the like. The particular carrier, diluent or other excipient used will depend upon the means and purpose for which the CBN is being applied. Solvents are generally selected based on solvents recognized by persons skilled in the art as safe (GRAS) to be administered to a mammal.

In general, safe solvents are non-toxic aqueous solvents such as water and other non-toxic solvents that are soluble or miscible in water. Suitable aqueous solvents include water, ethanol, propylene glycol, polyethylene glycols (e.g., PEG 400, PEG 300), etc. and mixtures thereof. Acceptable diluents, carriers, excipients and stabilizers are nontoxic to recipients at the dosages and concentrations employed, and include buffers such as phosphate, citrate and other organic acids; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides and other carbohydrates including glucose, mannose, or dextrins; chelating agents such as EDTA; sugars such as sucrose, mannitol, trehalose or sorbitol; salt-forming counter-ions such as sodium; metal complexes (e.g., Zn-protein complexes); and/or non-ionic surfactants such as TWEENÔ, PLURONICSÔ or polyethylene glycol (PEG).

The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the CBN or aid in the manufacturing of the pharmaceutical product. The formulations may be prepared using conventional dissolution and mixing procedures.

Formulation may be conducted by mixing at ambient temperature at the appropriate pH, and at the desired degree of purity, with physiologically acceptable carriers, i.e., carriers that are non-toxic to recipients at the dosages and concentrations employed. The pH of the formulation depends mainly on the particular use and the concentration of compound, but may range from about 3 to about 8. Formulation in an acetate buffer at pH 5 is a suitable embodiment.

The CBN formulations can be sterile. In particular, formulations to be used for in vivo administration must be sterile. Such sterilization is readily accomplished by filtration through sterile filtration membranes.

The CBN ordinarily can be stored as a solid composition, a lyophilized formulation or as an aqueous solution.

The pharmaceutical compositions comprising a CBN can be formulated, dosed and administered in a fashion, i.e., amounts, concentrations, schedules, course, vehicles and route of administration, consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The "therapeutic amount" of the compound to be administered will be governed by such considerations, and is the minimum amount necessary to prevent, ameliorate, or treat the coagulation factor mediated disorder. Such amount is preferably below the amount that is toxic to the host or renders the host significantly more susceptible to bleeding.

The CBN can be formulated into pharmaceutical dosage forms to provide an easily controllable dosage of the drug and to enable patient compliance with the prescribed regimen. The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The pharmaceutical compositions may be in the form of a sterile injectable preparation, such as a sterile injectable aqueous or oleaginous suspension. This suspension may be formulated according to the known art using those suitable dispersing or wetting agents and suspending agents which have been mentioned above. The sterile injectable preparation may also be a sterile injectable solution or suspension in a non-toxic parenterally acceptable diluent or solvent, such 1,3-butanediol. The sterile injectable preparation may also be prepared as a lyophilized powder. Among the acceptable vehicles and solvents that may be employed are water, Ringer's solution and isotonic sodium chloride solution. In addition, sterile fixed oils may conventionally be employed as a solvent or suspending medium. For this purpose any bland fixed oil may be employed including synthetic mono- or diglycerides. In addition, fatty acids such as oleic acid may likewise be used in the preparation of injectables.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents.

The amount of CBN that may be combined with the carrier material to produce a single dosage form will vary depending upon the host treated and the particular mode of administration. For example, a time-release formulation intended for oral administration to humans may contain approximately 1 to 1000 mg of active material compounded with an appropriate and convenient amount of carrier material which may vary from about 5 to about 95% of the total compositions (weight:weight). The pharmaceutical composition can be prepared to provide easily measurable amounts for administration. For example, an aqueous solution intended for intravenous infusion may contain from about 3 to 500 g of the active ingredient per milliliter of solution in order that infusion of a suitable volume at a rate of about 30 mL/hr can occur.

The formulations may be packaged in unit-dose or multi-dose containers, for example sealed ampoules and vials, and may be stored in a freeze-dried (lyophilized) condition requiring only the addition of the sterile liquid carrier, for example water, for injection immediately prior to use. Extemporaneous injection solutions and suspensions are prepared from sterile powders, granules and tablets of the kind previously described. Preferred unit dosage formulations are those containing a daily dose or unit daily sub-dose, as herein above recited, or an appropriate fraction thereof, of the active ingredient.

The subject matter described herein includes the following embodiments:
1. A method of preparing a compound of Formula I,

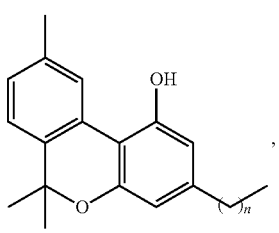

wherein, n is 1, 2, 3 or 4;

comprising,
contacting a compound of Formula II,

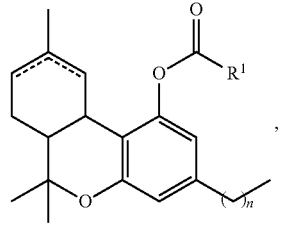

wherein,
n is 1, 2, 3 or 4; and
$R^1$ is an alkyl or aryl;
one of ===== is a double bond, the other is a single bond;
with an oxidant, optionally in the presence of a first solvent, to prepare a compound of Formula III,

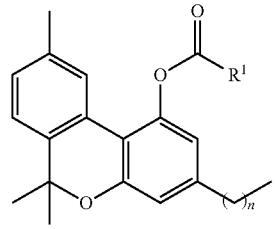

wherein,
n is 1, 2, 3 or 4; and
$R^1$ is an alkyl or aryl;
and,
contacting the compound of Formula III with a base in the presence of a second solvent to prepare a composition comprising a compound of Formula I.
2. The method of embodiment, wherein n is 2 or 4.
3. The method of embodiment 1 or 2, wherein n is 4.
4. The method of embodiment 1, 2 or 3, wherein $R^1$ is an optionally substituted straight or branched $C_{1-6}$ alkyl or optionally substituted $C_{6-10}$ aryl.
5. The method of embodiment 1, 2, 3 or 4, wherein $R^1$ is methyl, ethyl, n-propyl, isopropyl, n-butyl, sec-butyl, t-butyl, isobutyl, pentyl, neopentyl, or hexyl.
6. The method of embodiment 1, 2, 3, 4 or 5, wherein the $C_{6-10}$ aryl is selected from the group consisting of phenyl, indenyl and naphthalenyl.
7. The method of embodiment 1, 2, 3, 4, 5 or 6, wherein the $C_{6-10}$ aryl is naphthalenyl.
8. The method of embodiment 1, 2, 3, 4, 5 or 7, wherein the oxidant is $I_2$ or sulfur.
9. The method of embodiment 1, 2, 3, 4, 5, 6, 7 or 8, wherein the oxidant is present in an amount of about 1 equivalent to about 10 equivalents.
10. The method of embodiment 1, 2, 3, 4, 5, 6, 7, 8 or 9, wherein the oxidant is present in an amount of about 1.5 equivalents to about 4.5 equivalents.
11. The method of embodiment 1, 2, 3, 4, 5, 6, 7, 8, 9 or 10, wherein the base is an alkali metal hydroxide.
12. The method of embodiment 1, 2, 3, 4, 5, 6, 7, 8, 9, 10 or 11, wherein the alkali metal hydroxide is LiOH.

13. The method of embodiment 1, 2, 3, 4, 5, 6, 7, 8, 9, 10, 11 or 12, wherein the oxidant is iodine.

14. The method of embodiment 1, 2, 3, 4, 5, 6, 7, 8, 9, 10, 11, 12 or 13, wherein the method does not comprise separating a compound of Formula I and/or Formula III by column chromatography.

15. The method of embodiment 13, further comprising crystallizing a compound of Formula III, the crystallizing comprising, contacting the compound of Formula III with at least two crystallizing solvents to prepare a purified compound of Formula III.

16. The method of embodiment 15, wherein the purified compound of Formula III has a purity (AUC) of at least 80%.

17. The method of embodiment 15, wherein the purified compound of Formula III has a purity (AUC) of at least 90%.

18. The method of embodiment 15, wherein the purified compound of Formula III has a purity (AUC) of at least 99%, such as, 99.1%, 99.2%, 99.3%, 99.4%, 99.5%, 99.6%, 99.7%, 99.8%, 99.9%, or 99.99%.

19. The method of embodiment 15, 16, 17 or 18, wherein the at least two crystallizing solvents are selected from the group consisting of methanol, ethanol, isopropanol, acetone.

20. The method of embodiment 19, wherein the solvents are acetone and methanol.

21. The method of embodiment 15, 16, 17, 18, 19 or 20, wherein the solvents are in a ratio of about 1:1.

22. The method of embodiment 15, 16, 17, 18, 19, 20 or 21, wherein:
    n is 4;

R¹ is

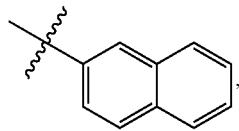 [SMILES: *c1ccc2ccccc2c1]

wherein

is the point of attachment to the carbonyl;
    the first solvent is present and is toluene;
    the contacting a compound of Formula II is at reflux;
    the method further comprising:
        filtering the compound of Formula III to prepare a first solid;
        contacting the first solid with acetone (about 1 volume) and heating to about 55° C. to form a first solution;
        contacting the first solution with MeOH (about 2 volumes), and heating to about 58° C. to form a second solution;
        allowing the second solution to cool to about 20° C. to prepare a second solid;
        filtering the second solid to prepare a filtered second solid and a filtrate;
        preparing a third solid from the filtrate and re-crystallizing from acetone/methanol (about 1:1) to prepare a fourth solid;
        combining the filtered second solid and the fourth solid and re-crystallizing from acetone/methanol (about 2:1) to prepare a purified compound of Formula III from the combined solids.

23. The method of embodiment 15, 16, 17, 18, 19, 20, 21 or 22, wherein the purified compound of Formula III has a purity above about 99% purity (AUC).

24. The method of embodiment 22 or 23, where the contacting the compound of Formula III with a base, comprises:
    contacting the purified compound of Formula III with LiOH to prepare a compound of Formula I, having the structure:

25. The method of embodiment 15, 16, 17, 18, 19, 20, 21, 22, 23 or 24, wherein compound 1 has a purity above about 99% purity (AUC).

26. The method of embodiment 8, wherein the oxidant is sulfur.

27. The method of embodiment 26, wherein the method is a one-pot preparation of a compound of Formula I.

28. The method of embodiment 27, wherein the method does not comprise separating a compound of Formula I and/or Formula III by column chromatography.

29. The method of embodiment 26, 27 or 28, further comprising a fractional distillation of the composition comprising a compound of Formula I to prepare a purified compound of Formula I.

30. The method of embodiment 29, wherein the fractional distillation comprises:
    heating the composition at a temperature of from about 210° C. to about 219° C. and collecting a fraction.

31. The method of embodiment 29 or 30, wherein the fractional distillation further comprises:
    heating the composition at a temperature of from about 226° C. to about 230° C. and collecting a fraction.

32. The method of embodiment 29, 30 or 31, wherein the fractional distillation further comprises:
    heating the composition at a temperature of at least 245° C. and collecting at least one fraction.

33. The method of embodiment 26, 27, 28, 29, 30, 31 or 32, wherein the compound of Formula I has a purity (AUC) of at least 99%.

34. A crystalline cannabinol. A crystalline cannabinol that is formed by a method of any one of embodiments 1-32.

35. A crystalline cannabinol having the PXRD as shown in FIG. 15.

36. A crystalline cannabinol of any above embodiment having a particle size: D10 of about 26 µm, D50 of about 337 µm, and/or D90 of about 1330 µm; or a crystalline cannabinol of any above embodiment having a particle size: D10 of about 16 µm, D50 of about 56 µm, and/or D90 of about 156 µm. The particle size can provide desirable properties to the solid form.

37. A method of preparing crystalline cannabinol comprising at least one heat and cooling cycle of an amorphous cannabinol as prepared by any method of embodiments 1-33, wherein the temperature of the cycle(s) is from about −20° C. to about 60° C. and a crystalline cannabinol is prepared.

38. The method of embodiment 37, wherein the amorphous cannabinol is an oil.

39. A method of preparing crystalline cannabinol comprising from two to twenty heat and cooling cycles of an amorphous cannabinol as prepared by any method of embodiments 1-33, wherein the temperature in each cycle is from about −20° C. to about 60° C. and a crystalline cannabinol is prepared.

40. The method of embodiment 39, wherein the amorphous cannabinol is an oil.

41. The method of embodiment 39, further comprising contacting the amorphous cannabinol with one or more solvents.

42. The method of embodiment 41, wherein the one or more solvents is/are a non-polar solvent.

43. The method of embodiment 41, wherein the one or more solvents is/are selected from the solvents in Table 7.

44. The method of embodiment 42, wherein the solvent is selected from the group consisting of n-heptane, iso-octane and n-pentane.

45. The method of embodiment 44, wherein the solvent is iso-octane.

46. The method of embodiment 43, wherein the solvent is n-pentane and a second solvent is selected from the solvents in Table 7.

46. The method of embodiment 45, wherein the second solvent is 1-propanol or 2-propanl.

47. The method of any above embodiments 1-32 and 33-46 further comprising contacting an amorphous cannabinol with a seed of crystalline CBN in the presence of one or more solvents.

48. The method of embodiment 47, wherein the one or more solvents is/are a non-polar solvent.

49. The method of embodiment 47, wherein the one or more solvents is/are selected from the solvents in Table 7.

50. The method of embodiment 49, wherein the solvent is selected from the group consisting of n-heptane, iso-octane and n-pentane.

51. The method of embodiment 50, wherein the solvent is n-pentane.

52. The method of any above embodiment further comprising crystallizing CBN from an amorphous CBN, the crystallizing comprising dissolving the amorphous CBN in a non-polar solvent to form a solution, and cooling the solution.

53. The method of embodiment 52, wherein the non-polar solvent is iso-octane.

53. A method of crystallizing CBN from an amorphous CBN, the crystallizing comprising dissolving the amorphous CBN in a non-polar solvent to form a solution, and cooling the solution.

54. The method of embodiment 53, wherein the non-polar solvent is a branched hydrocarbon having a MW above pentane.

55. The method of embodiment 54, wherein the branched non-polar solvent is iso-octane.

56. A method of recrystallizing CBN comprising:
Dispersing CBN solids in 1-10 volumes, 2-5 volumes or 3.5 volume, of a high MW non-polar, branched hydrocarbon solvent at about room temperature to form a mixture;
Heating the mixture to about 70° C. to dissolve the CBN solids to form a solution;
Cooling the solution to about 40° C.;
Seeding the said solution at about 40° C. with a CBN seed (for example, 1 wt %) to prepare a suspension;
Allowing the suspension to warm to about 40° C. with stirring;
Allowing the suspension to stir at about 40° C. for at least 60 min;
Cooling the suspension to about 10° C. for about 120 min;
Separating the solid material via filtration from the suspension;
Washing the solid material with about 1-10 volumes, 2-6 volumes, or 2 volumes of a second solvent at about −20° C.; and
Drying the solid material at about 40° C. under vacuum for at least 12 h to obtain a crystalline CBN.

57. The method of embodiment 56, wherein the high MW non-polar, branched hydrocarbon solvent is iso-octane or n-heptane.

58. The method of embodiment 57, wherein the yield of crystalline CBN is above 95%.

59. The method of embodiment 58, wherein the high MW non-polar, branched hydrocarbon solvent is iso-octane.

60. The method of embodiment 59, wherein the second solvent is a high MW non-polar, branched hydrocarbon solvent.

61. The method of embodiment 60, wherein the second solvent is iso-octane.

The disclosed subject matter is further described in the following non-limiting Examples. It should be understood that these Examples, while indicating preferred embodiments of the invention, are given by way of illustration only.

EXAMPLES

Example 1: Preparation of CBN by Method A

CBN was prepared by Method A utilizing sulfur as the oxidant as depicted above in Scheme 3.

Step 1-A: D9-THC-NE (D9-THC-Naphthoylester) and 2.2 molar equivalents of Sulfur are heated to about 250° C. without solvent under a gentle nitrogen purge and equipped with a bleach scrubber. After 60-90 minutes, the reaction vessel was cooled to 60° C. The reaction mixture was a dark-red brown color.

Step 1-B: In the same reaction pot, CBN-Naphthoylester prepared in Step 1-A was saponified in THF/MeOH/Water with Lithium-hydroxide to the free CBN-NE. The reaction mixture was stirred for about 1 hour at 37-42° C. T-butyl methyl ether was added to the reaction mixture. The organic layer was washed with a solution of sodium carbonate and sodium ascorbate in water. The organic layer was washed by sodium carbonate in water. Note that this volume was double the volume of the initial wash. The organic layer was washed with NaCl in water twice. Activated Carbon was added to the organic layer. The activated carbon/reaction mixture slurry was heated to about 60° C. and stirred for about 1 hour. The mixture was cooled to room temperature and filtered. The Solution was a lighter red brown color after carbon treatment.

The wet cake was washed with t-butyl methyl ether to remove more product from the carbon cake. The solvents are removed via distillation to afford an oily crude product.

At a warmer temperature (e.g. at 60-70° C.), the crude CBN oil was poured and blended into silica gel to form a homogenous mixture, which was subjected to a fresh silica gel pad pre-loaded in a column. The product was flashed out using a mixture of n-heptane and ethyl acetate as the eluent. Fractions are combined based on HPLC analysis. The solvents were removed to afford a light brown crude oil. The crude oily product was transferred to a 3-L 1-neck round bottom flask and distilled to further remove the solvents (A final temperature of 100-150° C. is reached with a diaphragm vacuum pump).

After the removal of all the solvents, the distillation was continued with a fractional distillation head and a high vacuum oil pump (e.g. 0-1.0 mbar). The first fraction (~15%) was collected at a temperature between 210-219° C. The second fraction (~70%), a light yellow-clear oily product, was collected at a temperature between 226-230° C. The final fraction (~15%) was collected at 245° C. or higher. The fractions are tested by HPLC. Distillation may be repeated if necessary to achieve the desired purity.

Example 2: Preparation of CBN by Method A

Figure 1:
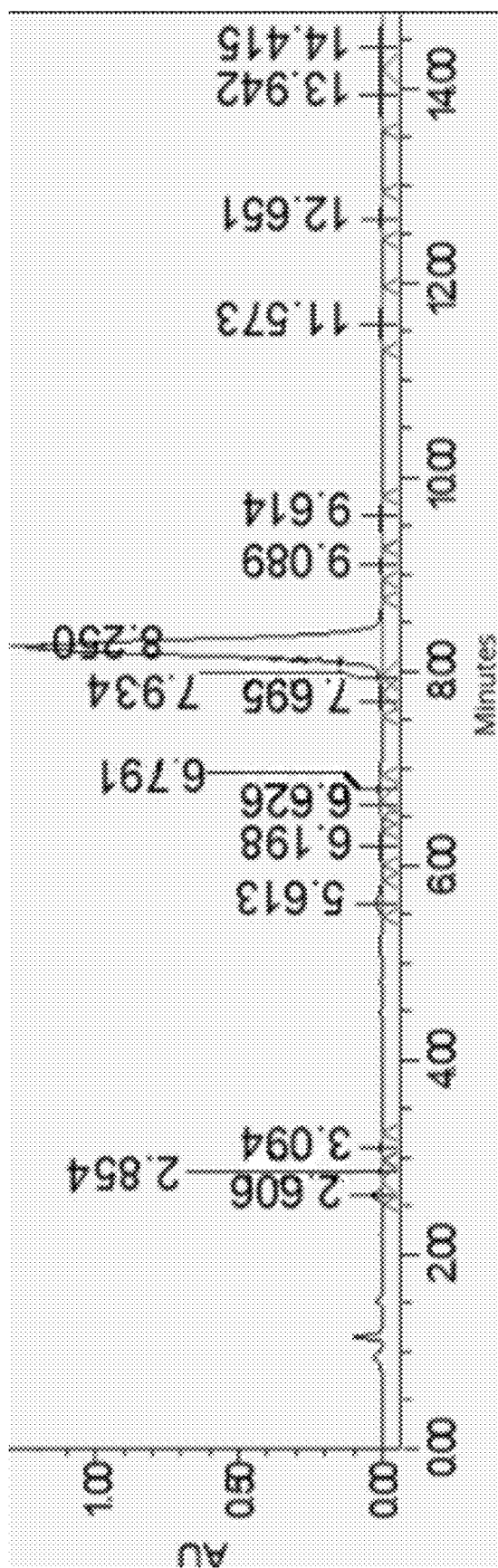
FIG. 1 depicts a HPLC chromatogram of the product of a sulfur oxidation of D9-THC-NE to CBN-NE by a method described herein.

In a 250 mL 3-neck round bottom flask equipped with nitrogen blanket and mechanical stirrer was added D9-THC-NE (789 g). Sulfur (Sigma) was added (118.75 g, 2.2 equiv.). The reaction was heated at 250° C. Melt began around 50° C. and the mixture was clear at about 100° C. The reaction was cooled to about 100° C. FIG. 1 depicts a HPLC chromatogram at completion of reaction around 1 hour. Table 1 shows the chromatogram peaks.

TABLE 1

| | Retention Time | Area | % Area | Height |
|---|---|---|---|---|
| 1 | 2.606 | 164558 | 1.10 | 40471 |
| 2 | 2.854 | 18021 | 0.12 | 4144 |
| 3 | 3.094 | 33704 | 0.22 | 7013 |
| 4 | 5.613 | 196793 | 1.31 | 23181 |
| 5 | 6.198 | 59591 | 0.40 | 5184 |
| 6 | 6.626 | 25076 | 0.17 | 3858 |
| 7 | 6.791 | 89573 | 0.60 | 10224 |
| 8 | 7.695 | 31705 | 0.21 | 3586 |
| 9 | 7.934 | 73320 | 0.49 | 9603 |
| 10 | 8.250 | 14038440 | 93.43 | 1245020 |
| 11 | 9.089 | 10083 | 0.07 | 1038 |
| 12 | 9.614 | 21333 | 0.14 | 1455 |
| 13 | 11.573 | 74404 | 0.50 | 4724 |
| 14 | 12.651 | 28563 | 0.19 | 1851 |
| 15 | 13.942 | 102913 | 0.68 | 5962 |
| 16 | 14.415 | 57678 | 0.38 | 2628 |

Figure 2:
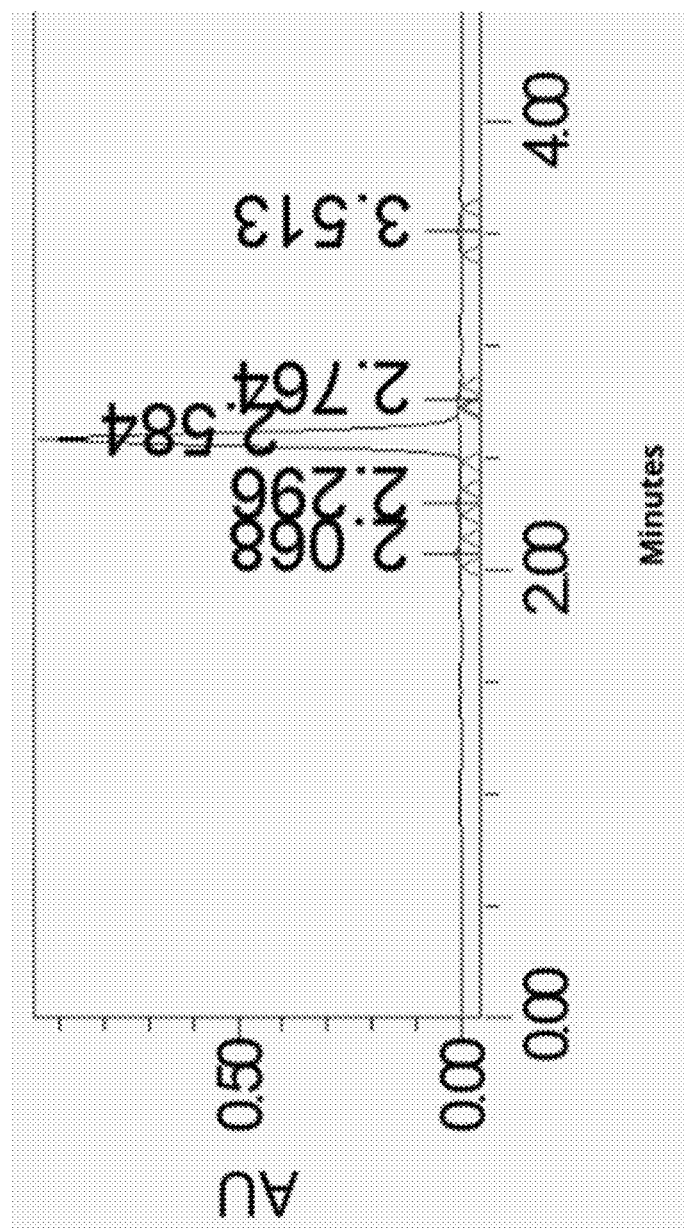
FIG. 2 depicts a HPLC chromatogram of the product of a hydrolysis of CBN-NE to CBN by a method described herein.

Hydrolysis of CBN-NE was performed by adding 3904 mL THF (Sigma-Aldrich) at 100° C., where after addition of the THF, the reaction had cooled to about 40° C. Methanol was added. The reaction temperature was about 39° C. To the reaction was added a solution of LiOH·H$_2$O (206.67 g, 2.93 equiv.) (Sigma-Aldrich) and sodium ascorbate (17.56 mmol, 10.89 g) (Alfa Aesar) in DI water (1656.54 mL. The reaction was stirred at 37-42° C. for about 1 hour. FIG. 2 depicts a HPLC chromatogram at completion of reaction. Table 2 shows the chromatogram peaks.

TABLE 2

| | Retention Time | Area | % Area | Height |
|---|---|---|---|---|
| 1 | 2.068 | 34326 | 0.88 | 10486 |
| 2 | 2.296 | 27378 | 0.70 | 7814 |
| 3 | 2.584 | 3803527 | 97.72 | 910151 |
| 4 | 2.764 | 6720 | 0.17 | 2387 |
| 5 | 3.513 | 20205 | 0.52 | 3703 |

Figure 3:
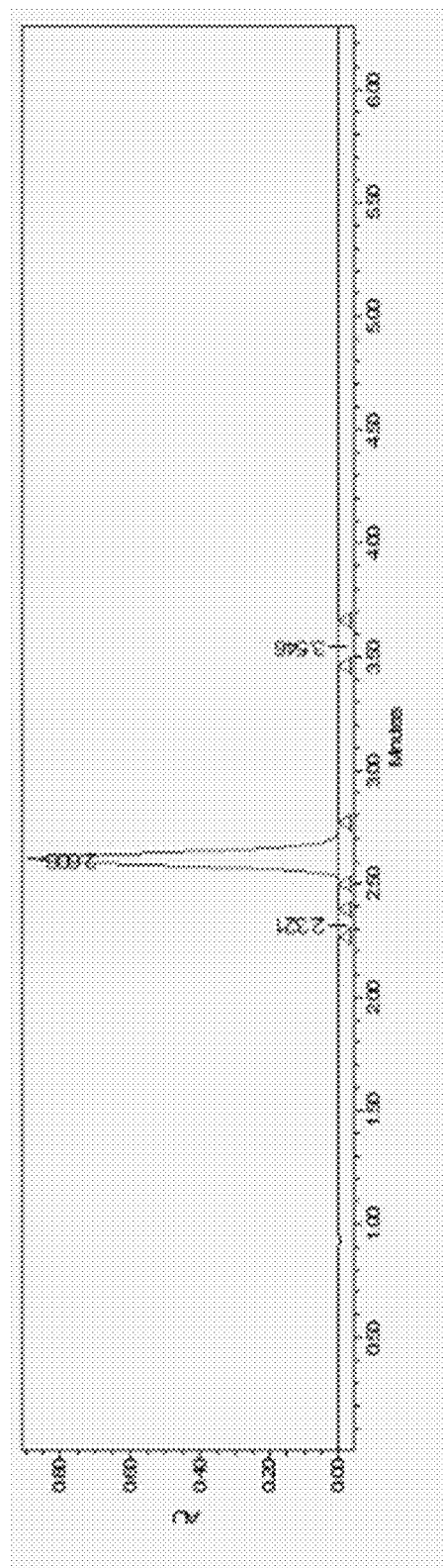
FIG. 3 depicts a HPLC chromatogram of CBN obtained by distillation as described herein.

The hydrolysis reaction product was subjected to a fractional distillation procedure. Fractional distillation was performed under vacuum (e.g., 0-3 mbar) at high temperature using a fractional distillation column. FIG. 3 depicts a HPLC chromatogram of a purified CBN fraction. Table 3 shows the chromatogram peaks.

TABLE 3

| Name | Retention Time | Area | % Area | Height |
|---|---|---|---|---|
| 1 | 2.321 | 9706 | 0.26 | 2698 |
| 2 | 2.608 | 3640146 | 99.37 | 867251 |
| 3 | 3.546 | 13537 | 0.37 | 2776 |

Example 3: Preparation of CBN by Method B

CBN was prepared by Method B utilizing I$_2$ as the oxidant as depicted in Scheme 4 above.

Figure 4:
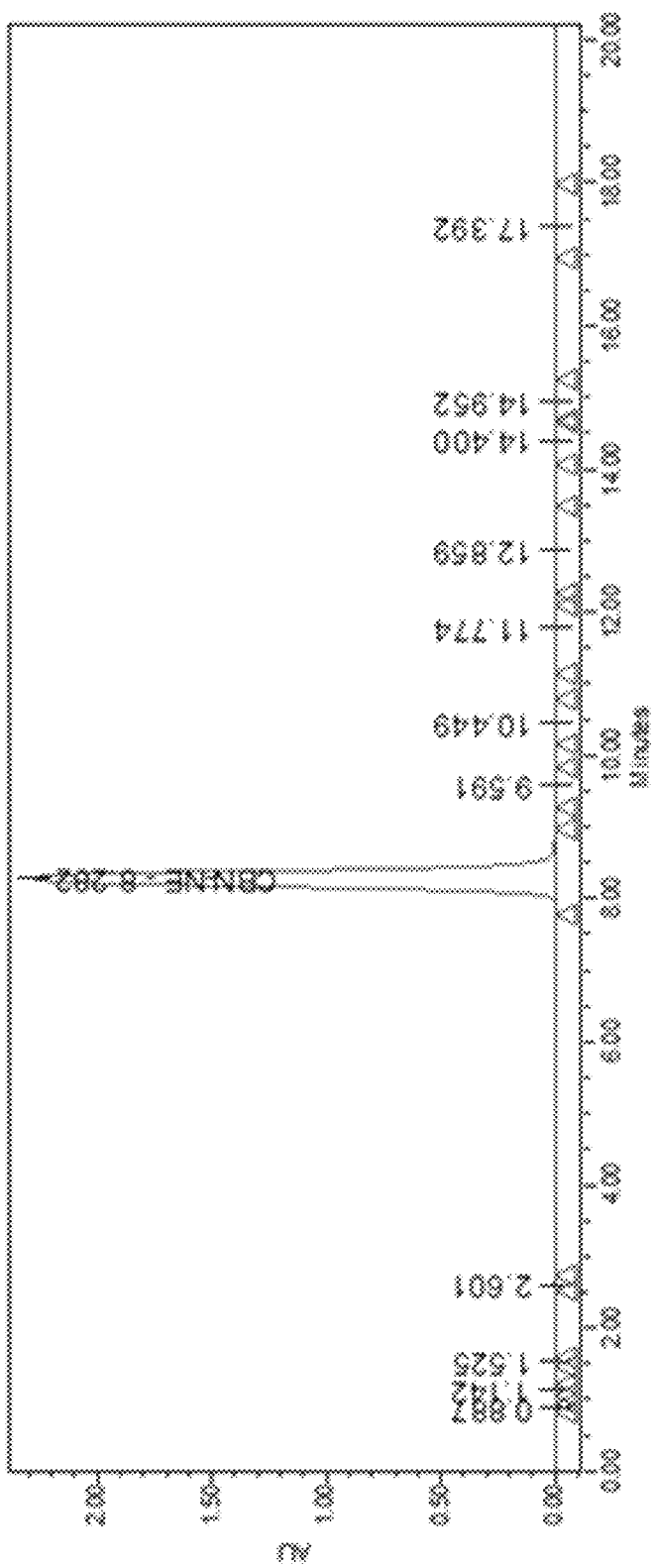
FIG. 4 depicts a HPLC chromatogram of the product of an iodine oxidation of D9-THC-NE to CBN-NE by a method described herein.

Step 1: Synthesis of CBN-NE. D9-THC-NE was dissolved in toluene (0.08-0.012 M, actual 0.1) and iodine 3.0 eq. was added. The reaction mixture was heated to reflux for about 48-72 hours (actual 48 hours). The outlet of the condenser was connected through a rubber tubing that was immersed in a saturated solution of sodium sulfite to trap iodine fumes. After reaction completion, it was cooled to 8.0° C. and a solution of sodium thiosulfate in water was added and stirred until iodine color discharges. Phased separation and the organic layer was washed with brine. Norit (activated carbon) was added and the mixture heated to about 70° C. for about 20 min. It was then filtered, and the filtrate was concentrated under vacuum. Acetone (about 1 volume) was added and heated to about 55° C., then methanol (about 2 volumes) was added and heated to about 58° C. It was then cooled to about 20° C. in about 20 minutes ramp and stirred at about this temperature for approximately an additional 30 minutes. Solid was filtered and washed with a mixture of acetone/methanol (1:2). Purity of solid was determined to be 97.7%. The filtrate was rotavapped and recrystallized from acetone/methanol (1:1). Both solids were combined and recrystallized from acetone/methanol (2:1) resulted in a purity (AUC) 99.4%. (FIG. 4). Table 4 shows the chromatogram peaks.

TABLE 4

| Peak Name | Retention Time (min) | Area | % Area | Height |
|---|---|---|---|---|
| 1 | | 0.887 | 5822 | 0.02 | 2333 |
| 2 | | 1.142 | 15402 | 0.05 | 5436 |
| 3 | | 1.525 | 1626 | 0.05 | 547 |
| 4 | | 2.601 | 16909 | 0.05 | 380.4 |
| 5 | CBN-NE | 8.282 | 33852139 | 99.37 | 2276632 |
| 6 | | 9.591 | 8902 | 0.03 | 616 |
| 7 | | 10.449 | 28804 | 0.03 | 1908 |
| 8 | | 11.774 | 30369 | 0.09 | 126.5 |
| 9 | | 12.859 | 50793 | 0.15 | 2018 |
| 10 | | 14.400 | 7967 | 0.02 | 489 |
| 11 | | 14.952 | 5613 | 0.02 | 321 |
| 12 | | 17.392 | 42318 | 0.12 | 1656 |

Figure 5:
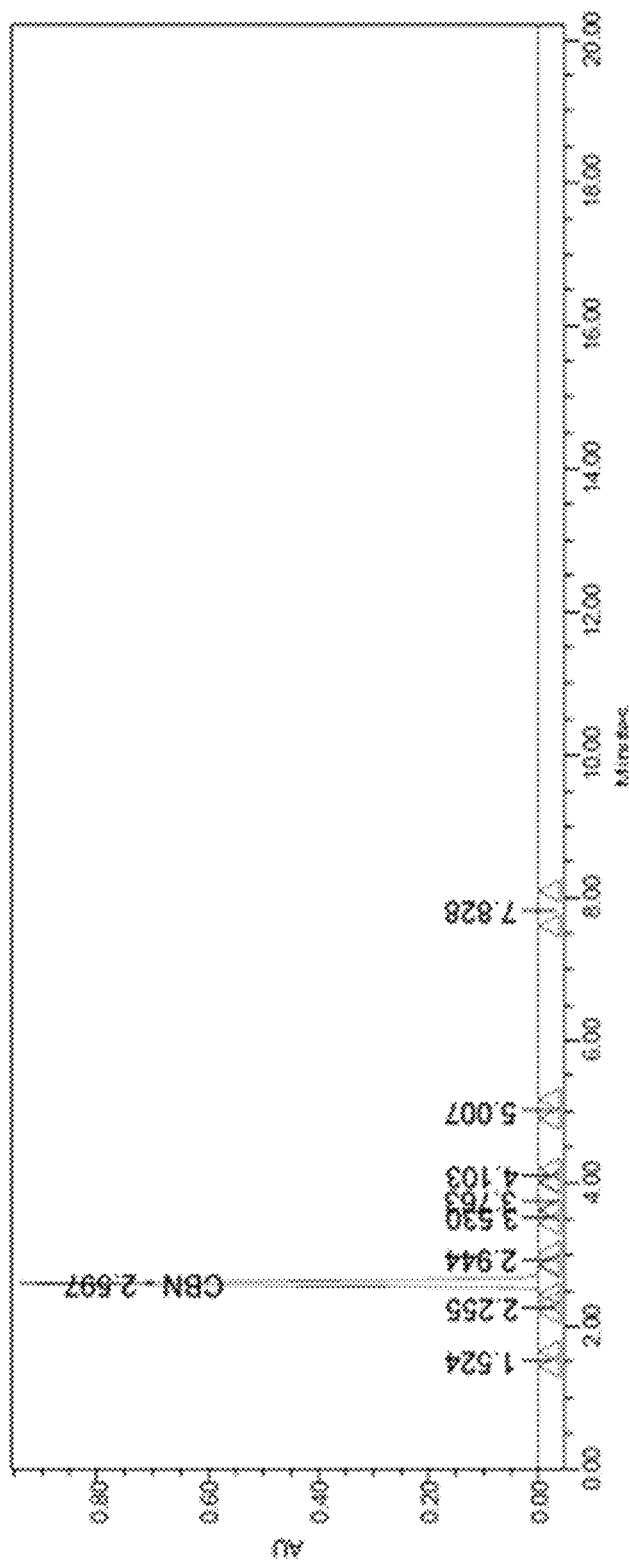
FIG. 5 depicts a HPLC chromatogram of the product of a hydrolysis of CBN-NE to CBN by a method described herein.

Step 2: Hydrolysis of CBN-NE to form CBN. CBN-NE (1.0 eq.) and sodium ascorbate (0.03 mol %) were dissolved in THF/MeOH. The solution was heated to about 39° C., then a solution of LiOH in water was added and heated at 37-42° C. for 1 h. It was then cooled to room temperature and extracted with MTBE. The organic layer was washed with a solution of Na2CO3/sodium ascorbate (2×). The organic layer was washed with brine, dried over magnesium sulfate and rotavapped. The product was a pale yellow oil (purity 99.4%). (FIG. 5). Table 5 shows the chromatogram peaks.

TABLE 5

| Peak | Name | Retention Time (min) | Area | % Area | Height |
|---|---|---|---|---|---|
| 1 | | 1.524 | 4450 | 0.12 | 1493 |
| 2 | | 2.255 | 291 | 0.01 | 85 |
| 3 | CBN | 2.597 | 37688971 | 99.37 | 911029 |
| 4 | | 2.944 | 2633 | 0.07 | 641 |
| 5 | | 3.530 | 408 | 0.01 | 77 |
| 6 | | 3.763 | 8330 | 0.22 | 1085 |
| 7 | | 4.103 | 650 | 0.02 | 125 |
| 8 | | 5.007 | 1838 | 0.06 | 285 |
| 9 | | 7.828 | 5577 | 0.15 | 508 |

Example 4: NMR Spectroscopy

Figure 11:
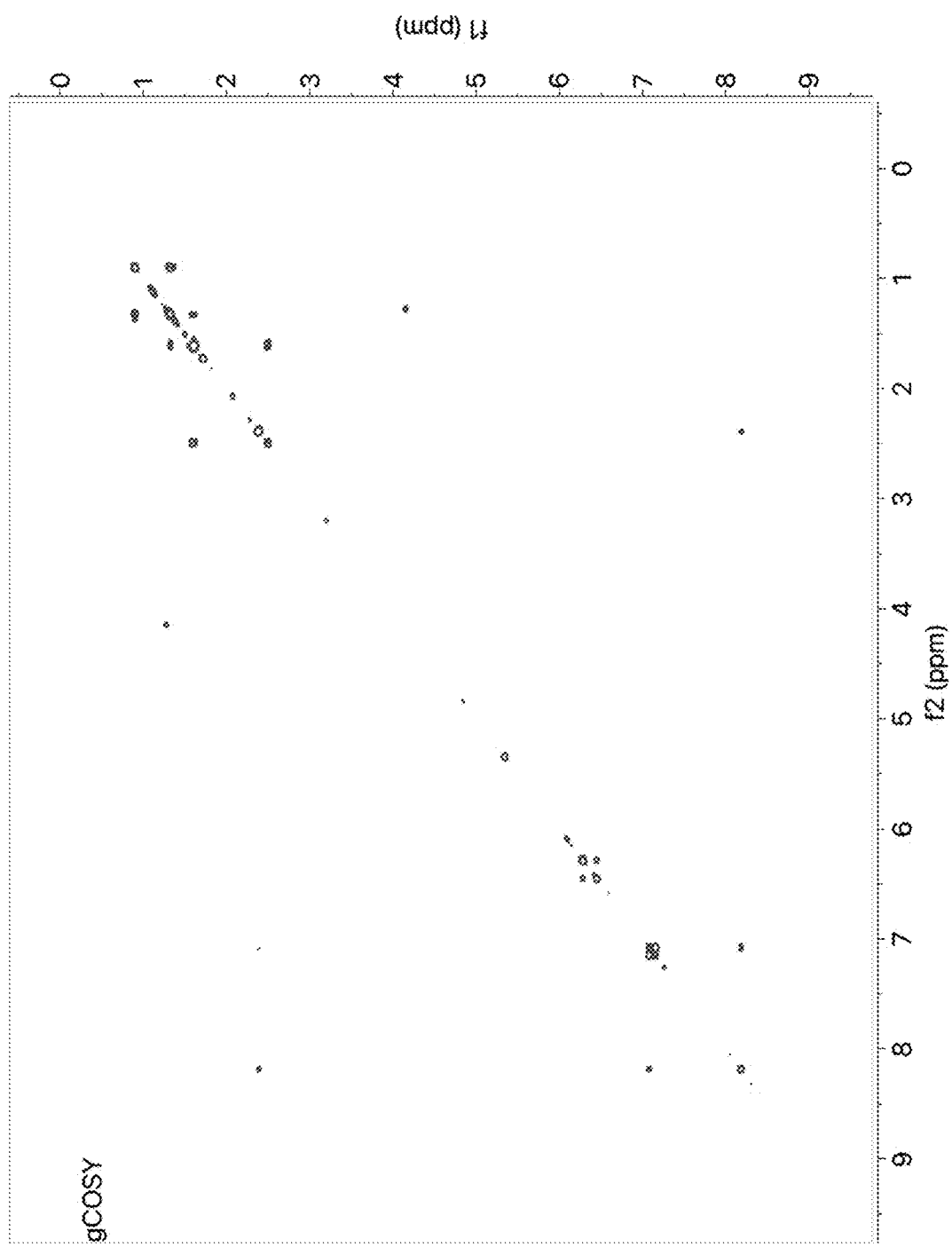
FIG. 11 depicts a 2-D gCOSY spectrum acquired in 400 increments of 2 transients each for a sample of CBN prepared by a method described herein.
Figure 12:
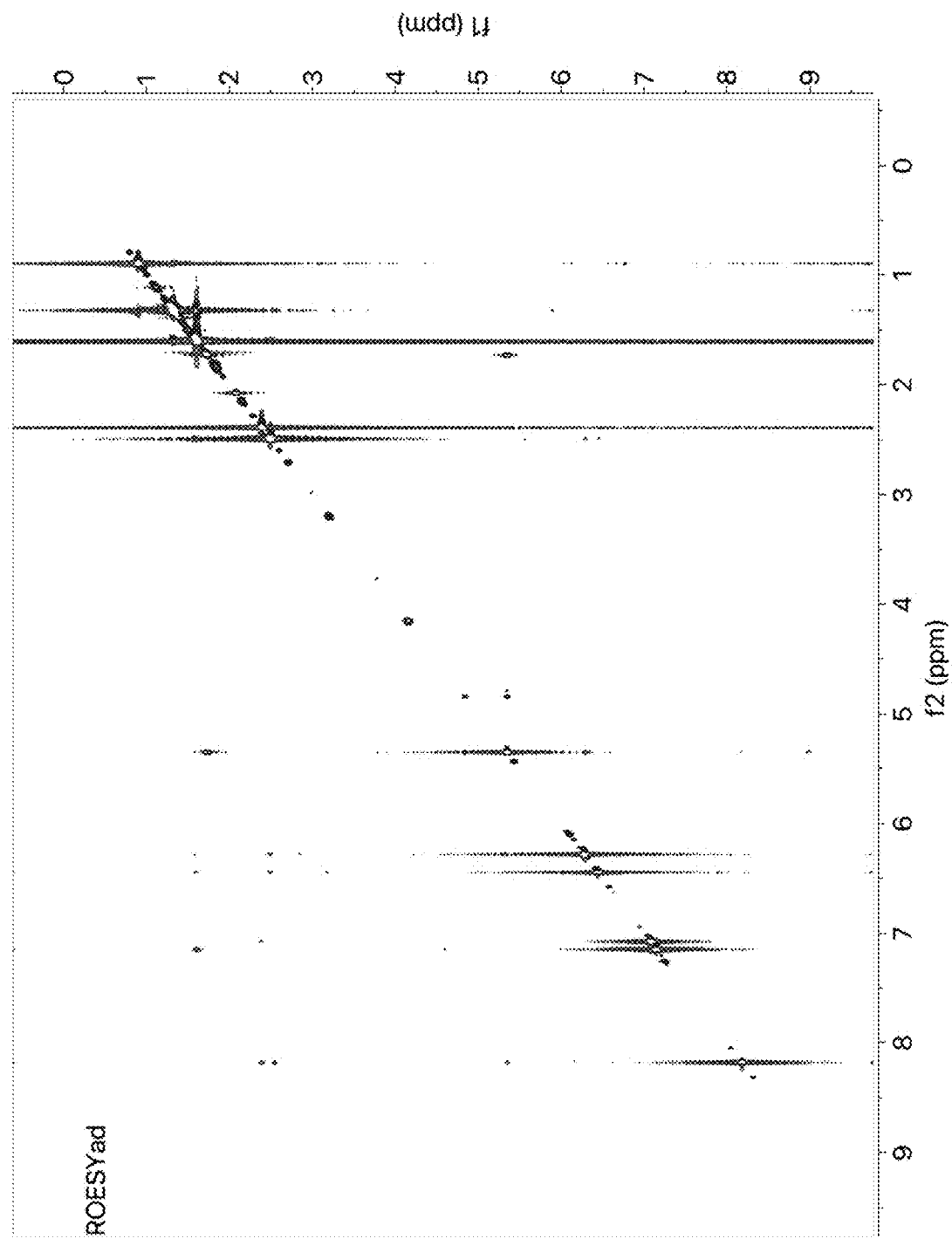
FIG. 12 depicts a ROESY spectrum acquired in 200 increments of 4 transients each for a sample of CBN prepared by a method described herein.
Figure 13:
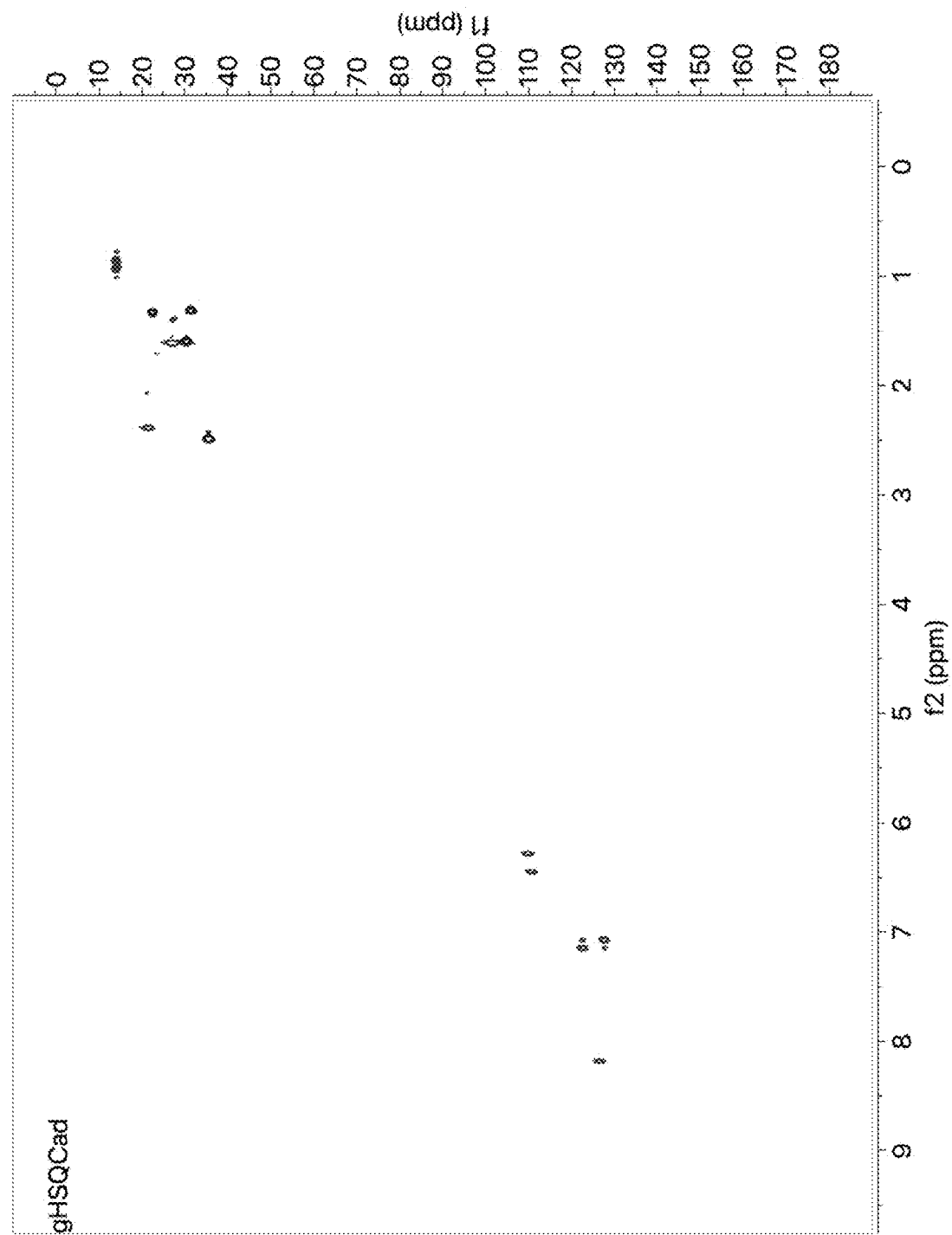
FIG. 13 depicts a gHSQCAD spectrum acquired in 128 increments of 8 transients each for a sample of CBN prepared by a method described herein.
Figure 14:
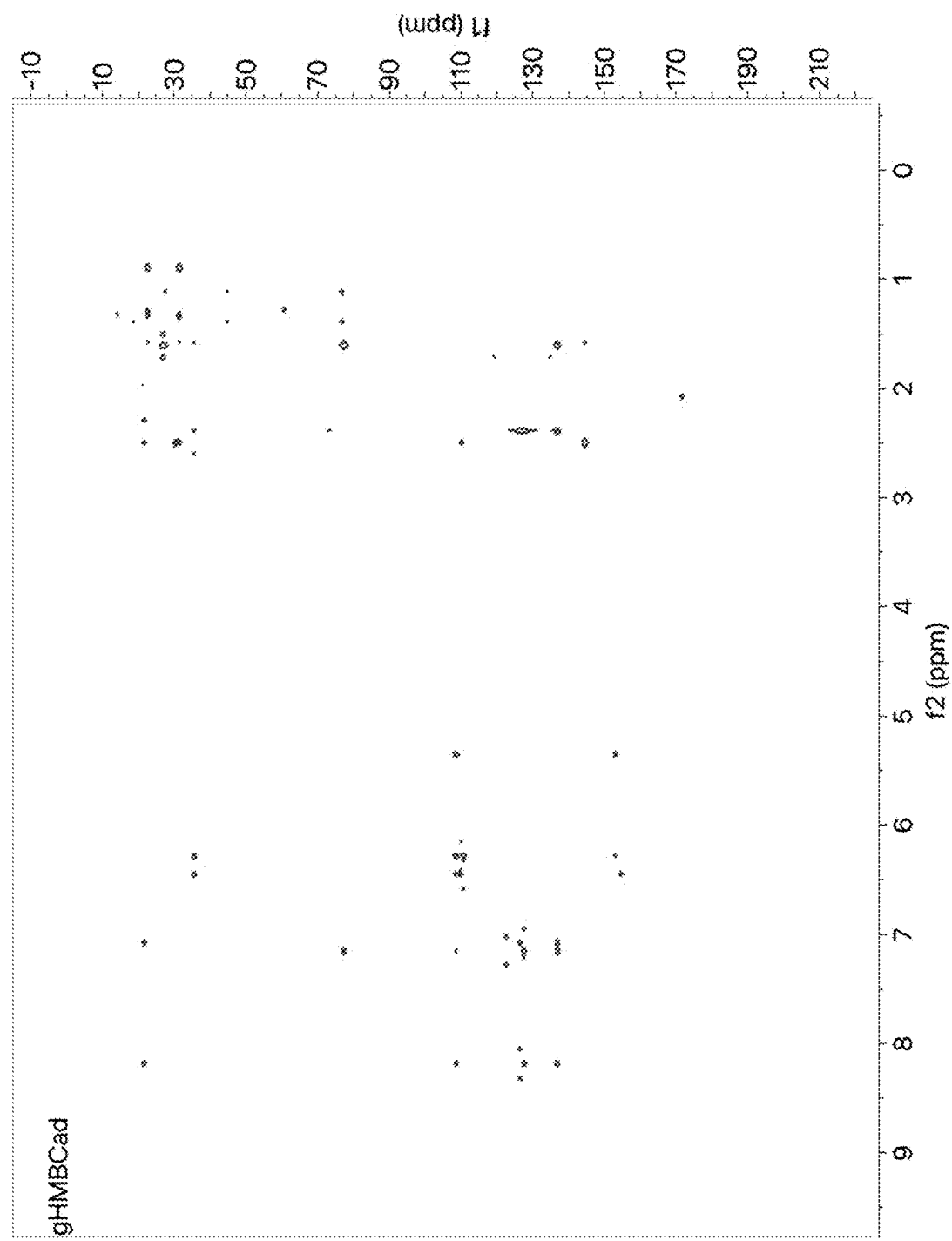
FIG. 14 depicts a gHMBCAD spectrum acquired in 200 increments of 16 transients each for a sample of CBN prepared by a method described herein.

Confirmation of the product was also performed by NMR. A sample from Method A was supplied and put into a 5-mm NMR tube in $CDCl_3$ solution. 1-D $^1H$, $^{13}C$ and $^{13}C$-DEPT NMR spectra (sample was analyzed neat on smart attenuated total reflectance (ATR) sampling accessory; Nicolet iS10 AKX1401499, as well as 2-D $^1H$-$^1H$-gCOSY and ROESYad, as well as $^1H$-$^{13}C$-gHSQCad and gHMBCad spectra were acquired on an Agilent Inova-600 MHz spectrometer at 25° C. using standard VNMRJ pulse sequences. Proton chemical shifts were measured relative to the residual $CDCl_3$ signal ($\delta_H$=7.26 ppm). Carbon chemical shifts were calculated using the absolute chemical shifts scale with reference to TMS at 0 ppm and a E value of 0.25145020. For the proton dimension, a spectral width of 6219 Hz was used, which was acquired in 8192 points in the 1-D spectrum and in 933 points in the 2-D spectra. Pulse width was 7.4 μs. The 2-D gCOSY spectrum (FIG. 11) was acquired in 400 increments of 2 transients each. The ROESY spectrum (FIG. 12) was acquired in 200 increments of 4 transients each. The gHSQCAD spectrum (FIG. 13) was acquired in 128 increments of 8 transients each and the gHMBCAD spectrum (FIG. 14) was acquired in 200 increments of 16 transients each. The spectral width in the indirect dimension was 30154.5 Hz (200 ppm) for gHSQCAD and 36183 (240 ppm) for gHMBC. The carbon spectrum was acquired with 704 transients at a spectral width of 37879 Hz, collected in 32768 points. For the DEPT spectra, the same parameters were used as for the carbon spectrum, except only 256 transients were acquired for each spectrum. All spectra were processed using MestreNova Version 12.0.3-21384.

Figure 6:
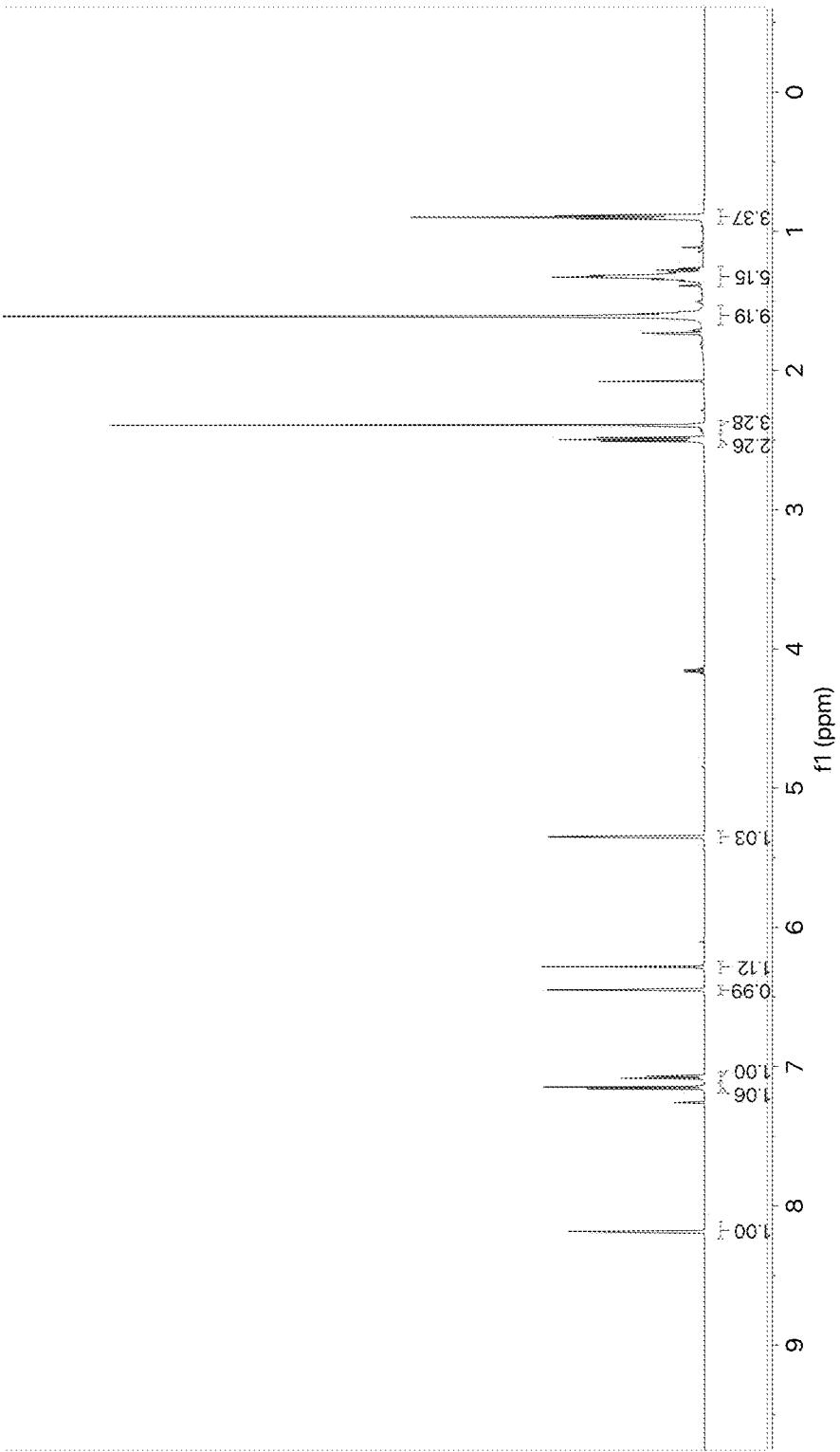
FIG. 6 depicts a 1D proton NMR spectrum of a sample of compound 1 prepared by a method as described herein.
Figure 7:
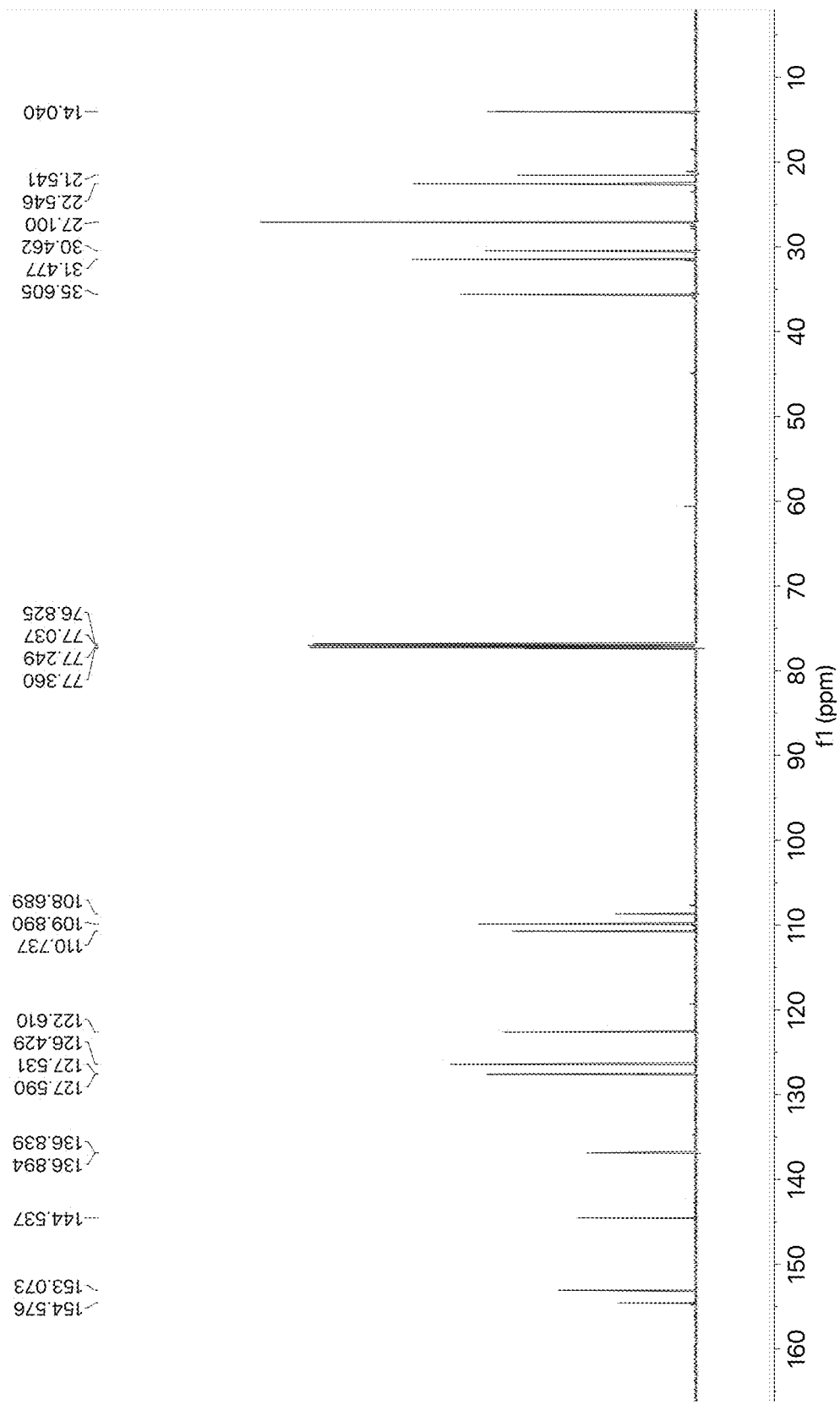
FIG. 7 depicts a 1D carbon NMR spectrum of a sample of compound 1 prepared by a method as described herein.
Figure 8:
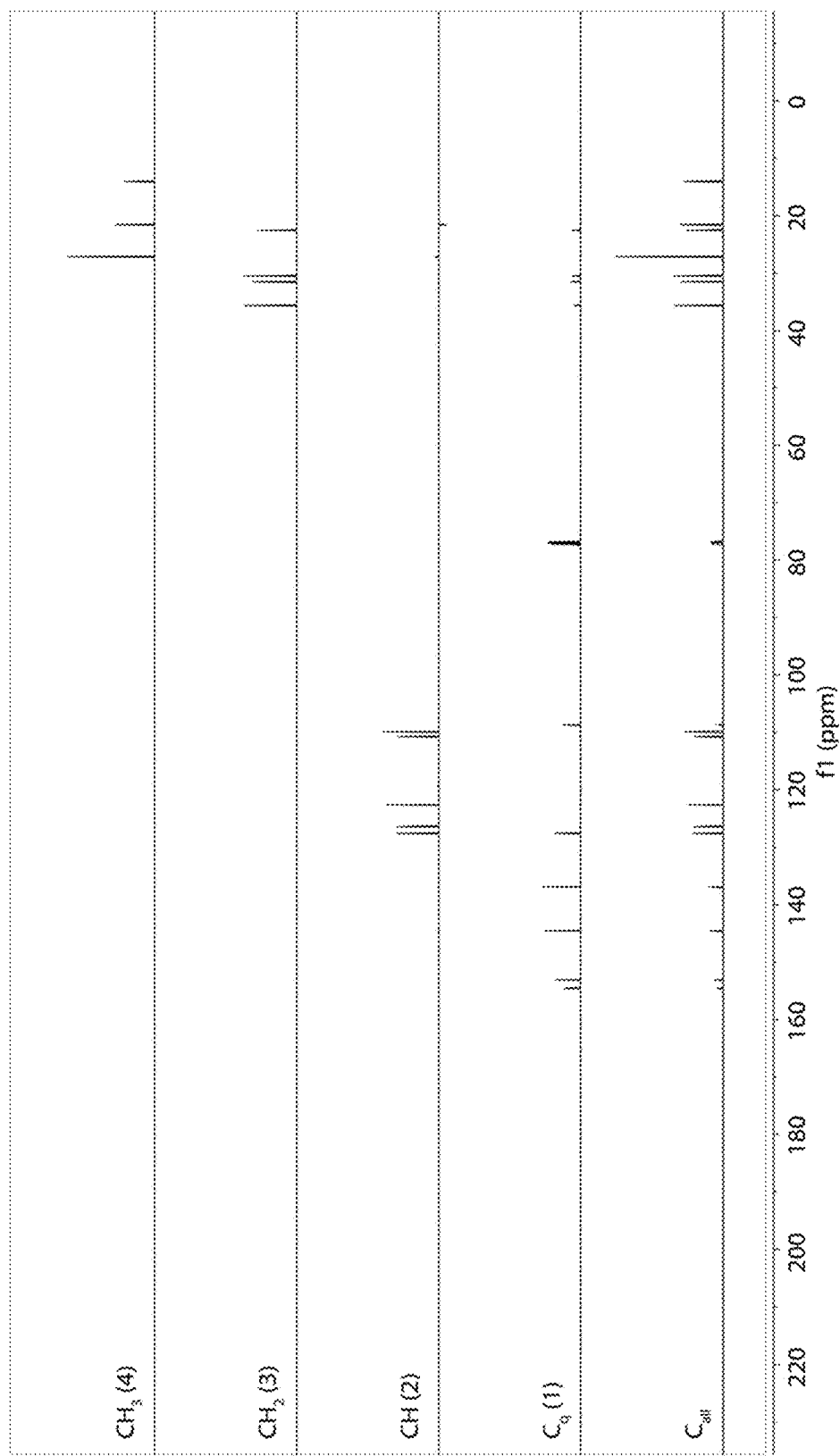
FIG. 8 depicts a DEPT spectra of a sample of compound 1 prepared by a method as described herein. The numbers in parentheses refer to the multiplicity that the detected peaks would have in a proton-coupled $^{13}$C spectrum.
Figure 9:
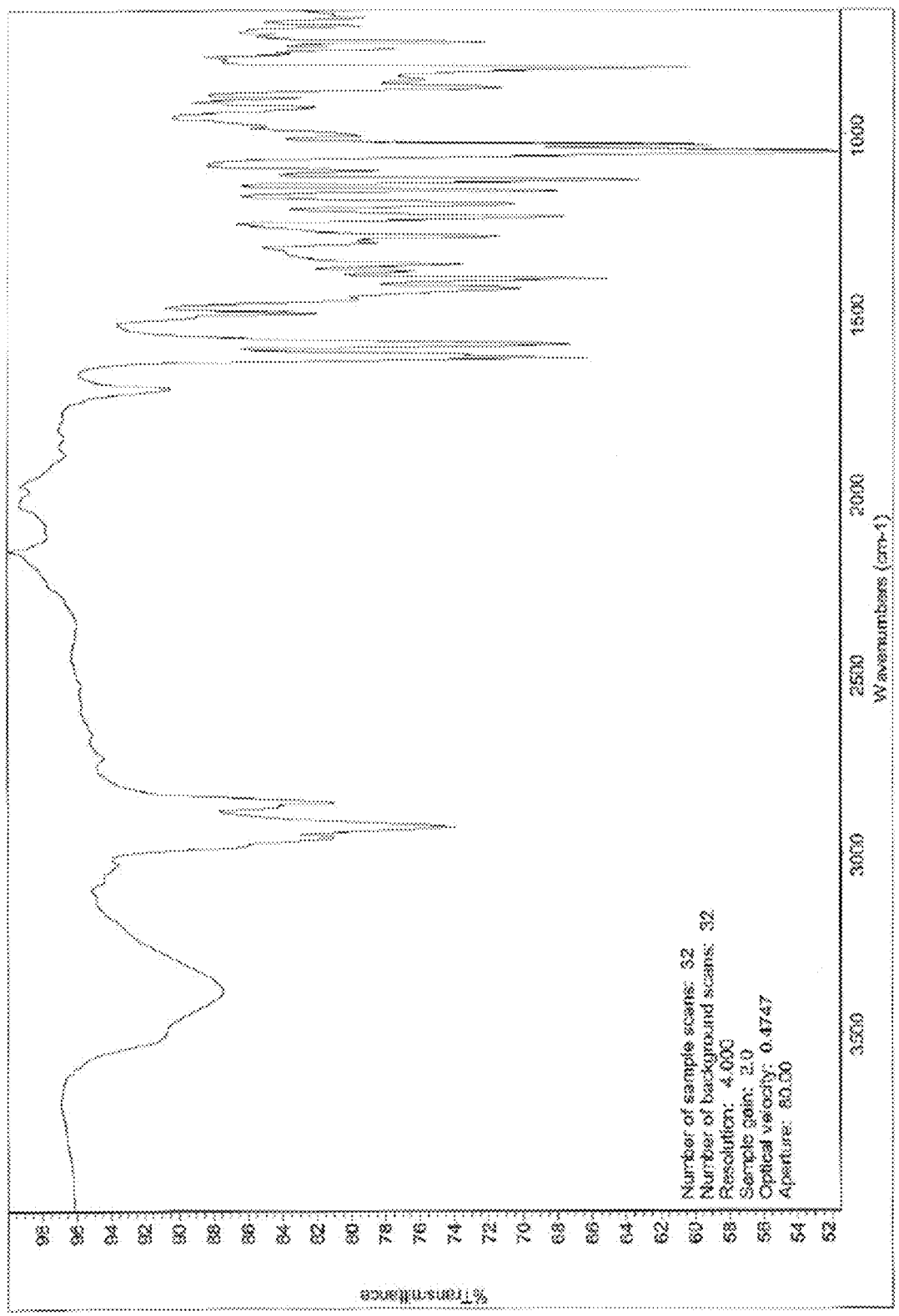
FIG. 9 depicts a FT-IR spectrum (LC/MS Waters Acquity UPLC H class with Acquity Qda) of CBN prepared by Method A as described herein.
Figure 10:
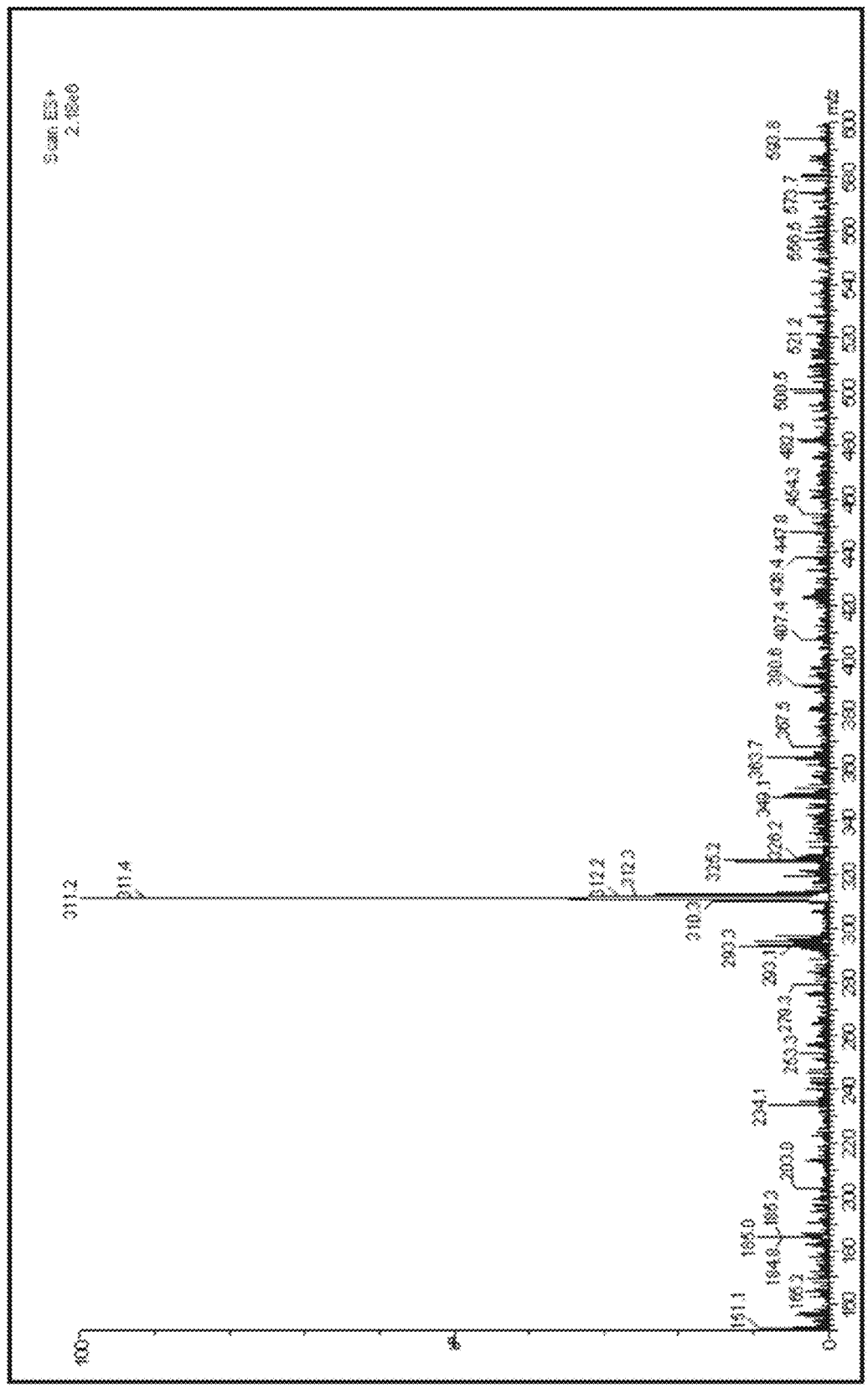
FIG. 10 depicts a mass spectrometry spectrum of CBN prepared by Method A as described herein.

The structure of compound 1 was confirmed by analysis of the 2-D gCOSY, gHSQCAD, and gHMBCAD spectra. The 1-D spectra (FIGS. 6 and 7) were acquired in order to obtain more precise measurements of the chemical shifts (Table 6), as the 1-D spectra can be acquired with greater resolution than the 2-D spectra. The gHSQCAD spectrum was acquired with multiplicity editing, which provides part of the same information as a set of 1-D $^{13}C$ DEPT spectra, in that methyl and methine groups appear as positive peaks and methylene protons as negative peaks. Additionally, DEPT spectra (FIG. 8) was acquired. The gHMBCAD spectrum provides the chemical shifts of all of the quaternary carbons and evidences the chemical shift assignment by displaying correlations between protons and carbons that are 2-3 bonds apart.

TABLE 6

Chemical shift assignments of sample of compound 1.

| Atom No. | Proton | Carbon | Multiplicity (from DEPT) | Integral | No. of Protons |
|---|---|---|---|---|---|
| 1(OH) | 5.349 | 153.07 | 1 | 1.03 | 1 |
| 2 | 6.283 | 109.89 | 2 | 1.12 | 1 |
| 3 | | 144.54 | 1 | | |
| 4 | 6.450 | 110.74 | 2 | 0.99 | 1 |
| 4a | | 154.58 | 1 | | |
| 6 | | 77.36 | 1 | | |
| 6a | | 136.84 | 1 | | |
| 7 | 7.153 | 122.61 | 2 | 1.06 | 1 |
| 8 | 7.077 | 127.59 | 2 | 1.00 | 1 |
| 9 | | 136.89 | 1 | | |
| 10 | 8.185 | 126.43 | 2 | 1.00 | 1 |
| 10a | | 127.53 | 1 | | |
| 10b | | 108.69 | 1 | | |
| 11 | 2.393 | 21.54 | 4 | 3.28 | 3 |
| 12, 13 | 1.611 | 27.10 | 4 | 9.19$^a$ | 6 |
| α | 2.495 | 35.61 | 3 | 2.26 | 2 |
| β | 1.600 | 30.46 | 3 | 9.19$^a$ | 2 |
| γ | 1.322 | 31.48 | 3 | 5.15 | 2 |
| δ | 1.331 | 22.55 | 3 | | 2 |
| ε | 0.899 | 14.04 | 4 | 3.37 | 3 |

$^a$This integral included protons β, 12, and 13, as well as the $H_2O$ peak in $CDCl_3$.

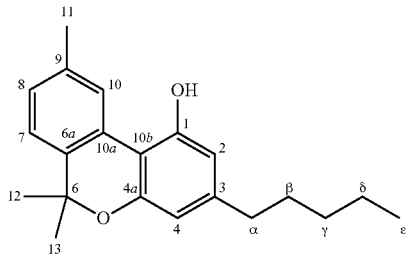

Example 5: Crystallization of CBN

The CBN oil prepared by methods described herein can be crystallized in a suitable solvent, and specifically non-polar solvents such as pentane, hexane, heptane, and iso-octane or may also be crystallized in a solvent mixture consisting of a non-polar solvent as the primary. solvent component and a polar solvent such as 1-propanol, 2-propanol, as a minor solvent component. The crystallization method also prepared a seed of crystalline CBN.

Numerous solvents were tried but did not result in formation of CBN crystals; however, the choice of the primary (non-polar) solvent for crystallization was found to be important in order to obtain a high yield of CBN solids. To maximize the yield, it was found helpful to cool the crystallization slurry to cold temperatures, ca. 10° C. The loss in yield was quantified in terms of the concentration of CBN in the mother liquor. Replacing n-heptane with another non-polar solvent, ca. iso-Octane was also studied; the CBN lost to the mother liquor when recrystallized in n-heptane was estimated to be approximately 4% w/w at 20° C. compared to only 1.5% w/w at 20° C. when recrystallized in iso-Octane. Crystallization of CBN oil with an assay purity of 100.5% w/w occurred via the heat and cooling cycle. CBN was not found to have multiple polymorphs. Table 7 shows the solvents selected for the solvent screen.

TABLE 7

| Solvent |
| --- |
| 1-propanol |
| 2-propanol |
| Acetone |
| MTBE |
| Ethanol |
| Methanol |
| N-heptane |
| Iso-Octane |
| N-pentane |
| Acetonitrile |
| Ethyl acetate |
| DCM |
| Toluene |
| THF |

Table 8 reports data including Mass Loss (ML) and Water Loss (WL).

TABLE 8

| Solvent | Crystallization volume | Boiling Point | Solubility at RT | MI losses (% w/w) | Wt. losses (% w/w) |
| --- | --- | --- | --- | --- | --- |
| Iso-Octane | 2.5 mL/g-CBN | 99° C. | 24.9 mg/mL | 1.4% wt | |
| n-Heptane | 2.5 mL/g-CBN | 98° C. | 33.43 mg/mL | 4.1% wt | 1.77% wt |
| 1-Propanol-Heptane (5/95) | 2.5 mL/g-CBN | −97° C. | >100 mg/mL | 77% wt | 20% wt |

Example 6: Recrystallization of CBN

CBN solids (67 g) were dispersed in 3.5 volumes of iso-octane at room temperature to form a solution. Heating the said solution to about 70° C. to dissolve all the CBN solids; Cooling the solution to about 40° C.; Seeding the said solution at about 40° C. with Cannabinol (1 wt %) to prepare a suspension; Allow the said suspension to warm to about 40° C. with stirring; Allow the said suspension to stir at 40° C. for at least 60 min; Cool the suspension to 10° C. over 120 min; Separate the solid material via filtration from the said suspension; Wash the solid material with 2 volumes iso-octane at about −20° C.; and Dry the solid material at 40° C. under vacuum for at least 12 h to obtain a crystalline composition comprising of cannabinol (65.4 g, 96.6% yield).

Example 7: Seeding of CBN Oil

Figure 19A:
FIGS. 19A and 19B show CBN crystal formation following seeding of the oil in the presence of the non-polar solvent, n-pentane.
Figure 19B:
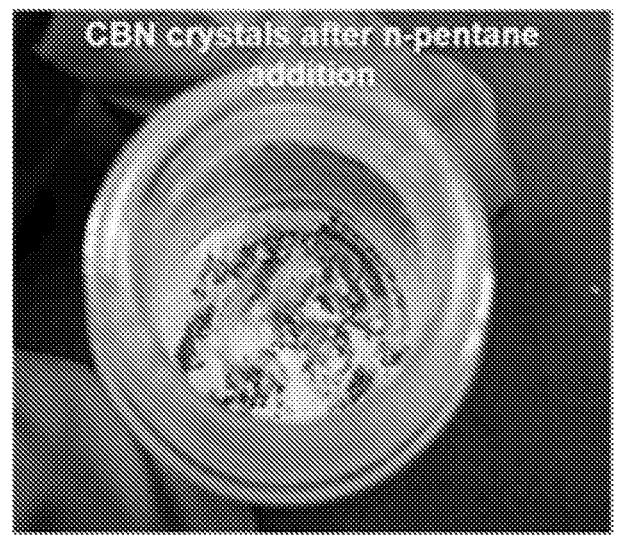

A seed of crystalline CBN as prepared by methods described herein was added to CBN oil, also prepared by methods described herein. The seed was added to the CBN oil in the presence of n-pentane. The mixture was sonicated. N-pentane may be acting as an antisolvent in the mixture. FIGS. 19A and 19B show CBN crystal formation following seeding of the oil in the presence of n-pentane.

Example 8: Particle Size Determination

The particle size distribution of a crystalline CBN was determined using a Malvern Particle Size Analyzer. Approximately 150 mg of solids was suspended in 0.1% PVP (Polyvinylpyrolidone) in water. Alternatively one can use povidone K29/32 (Mw ~58 kDa) or equivalent.

Instrument
  Malvern Mastersizer 3000
  Hydro MV sample dispersion unit
  Malvern Software Materials
  Povidone, or equivalent
  HPLC grade Water, or equivalent
  HPLC grade Acetone, or equivalent
  HPLC grade Isopropanol, or equivalent
  QAS4001 Glass Beads, or equivalent
  Filter paper GE Whatman, Grade 3, 70 mm, CAT No. 1003-070, or equivalent For the 0.1% Povidone (PVP) Solution Preparation: Dissolve 1 g of povidone in 1 L of Water (or equivalent ratio based on experimental needs). Stir for at least two hours. If necessary, filter to remove any residual undissolved PVP, ensure to utilize clean glassware for filtrate.

Sample Preparation for Malvern: Invert sample bottle end over end while rotating about the axis at a slight angle about 20 times to homogenize sample. When weighing samples, be cautious to transfer all material scooped onto spatula into the vial as not to bias the particle size distribution. Weight about 150 mg of NAB to a 20 mL i-chem vial, or equivalent. Then predisperse with 5 mL of 0.1% PVP Solution to wet all particles. Vortex 30 seconds. Use a pipette to gently mix prior to adding to Malvern. Rinse I-chem vial with 5 mL of 0.1% PVP in Water Solution and add rest of residual particulate to Malvern (Hydro MV). Note: The sample will be sonicated within Hydro MV dispersion unit. The initial % obscuration may increase or decrease during/after sonication depending on the nature of the material. If the obscuration does not remain within the 10%-20% range after pre-measurement delay (after 60 second sonication and 180 second delay), drain the dispersion unit (Hydro MV), complete the rinse procedure and re-prepare the sample at ±10-20 mg from the previous weight used.

Observation: The particle size for 90% of the CBN solids measured in dispersant solution was about 1330 micron. During recrystallization in iso-octane an apparent size reduction from 1330 micron particles to 156 micron particles occurred.

Figure 18A:
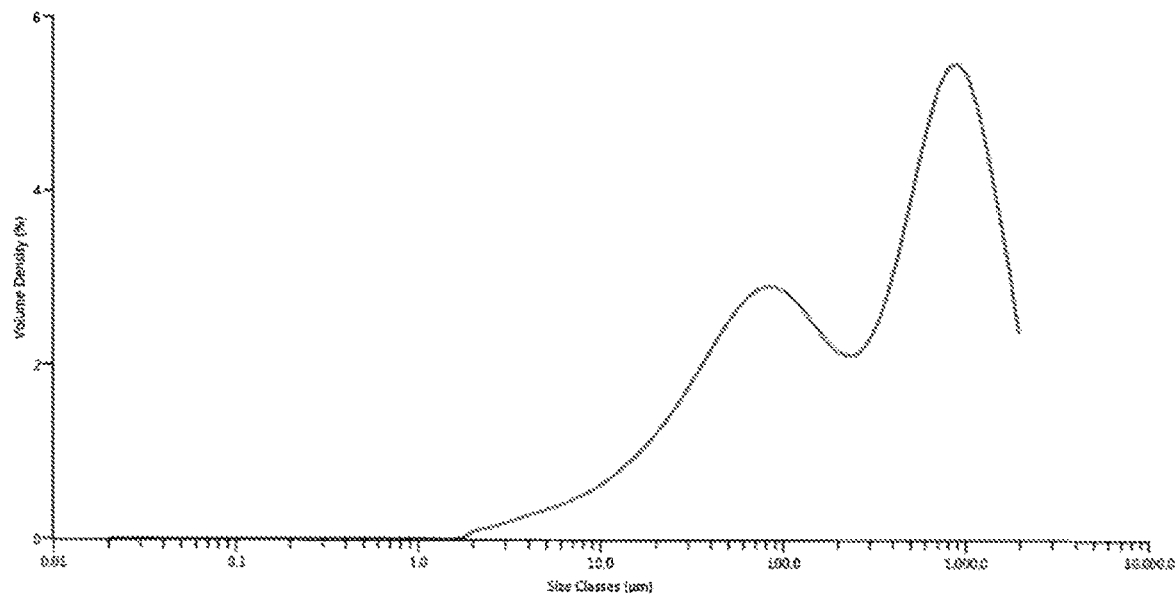
FIGS. 18A and 18B depict particle size distribution of crystalline CBN prepared by a method described herein.
Figure 18B:
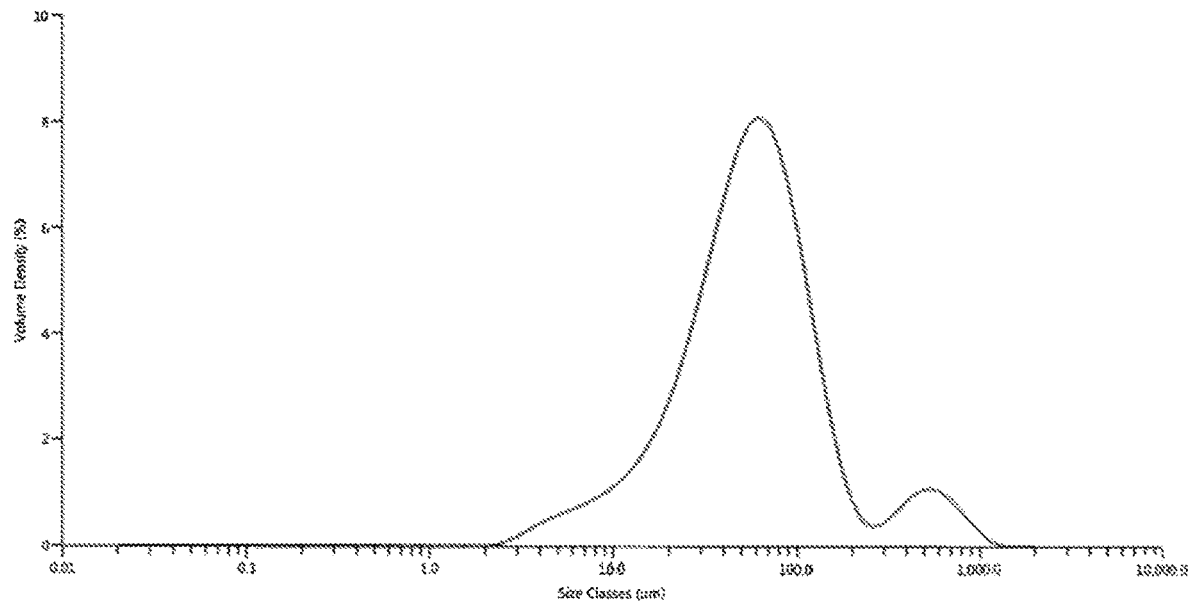

The data are shown in FIGS. 18A and 18B.
FIG. 18A:
  $D_v$ (10) 26.601 μm
  $D_v$ (50) 337.173 μm
  $D_v$ (90) 1330.06 μm
  Weighted Residual 0.34%
  Specific Surface Area 89.14 m/kg
  Uniformity 1.249
  Span 3.866
  Result units: Volume
  Laser Obscuration: 19.85%
  Low size: 0.02 μm
  High size: 2000:0 μm
FIG. 18B:
  $D_v$ (10) 16.484 μm
  $D_v$ (50) 56.670 μm
  $D_v$ (90) 156.434 μm
  Weighted Residual 0.18%
  Specific Surface Area 160.2 m$^2$/kg Uniformity 1.128
Span 2.470
Result units: Volume
Laser Obscuration: 19.39%
Low size: 0.02 μm
High size: 2000.0 μm The embodiments described above are intended to be merely exemplary, and those skilled in the art will recognize, or will be able to ascertain using no more than routine experimentation, numerous equivalents of specific compounds, materials, and procedures. All such equivalents are considered to be within the scope of the disclosure and are encompassed by the appended claims.

Citation or identification of any reference in this application is not an admission that such reference is available as prior art.

Efforts have been made to ensure accuracy with respect to numbers used (e.g. amounts, temperature, etc.) but some experimental errors and deviations should be accounted for.

When an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

Where a range of values is provided, it is understood that each intervening value, to the tenth of the unit of the lower limit, unless the context clearly dictates otherwise, between the upper and lower limit of the range and any other stated or intervening value in that stated range, is encompassed. The upper and lower limits of these small ranges which may independently be included in the smaller ranges is also encompassed, subject to any specifically excluded limit in the stated range. Where the stated range includes one or both of the limits, ranges excluding either or both of those included limits are also included.

Unless defined otherwise, technical and scientific terms used herein have the same meaning as commonly understood by one of ordinary skill in the art to which this subject matter belongs, and are consistent with: Singleton et al (1994) Dictionary of Microbiology and Molecular Biology, 2nd Ed., J. Wiley & Sons, New York, NY; and Janeway, C., Travers, P., Walport, M., Shlomchik (2001) Immunobiology, 5th Ed., Garland Publishing, New York.

The disclosures of all cited references including publications, patents, and patent applications are expressly incorporated herein by reference in their entirety.

Throughout this specification and the claims, the words "comprise," "comprises," and "comprising" are used in a non-exclusive sense, except where the context requires otherwise. It is understood that embodiments described herein include "consisting of" and/or "consisting essentially of" embodiments.

As used herein, the term "about," when referring to a value is meant to encompass variations of, in some embodiments ±50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Many modifications and other embodiments set forth herein will come to mind to one skilled in the art to which this subject matter pertains having the benefit of the teachings presented in the foregoing descriptions and the associated drawings. Therefore, it is to be understood that the subject matter is not to be limited to the specific embodiments disclosed and that modifications and other embodiments are intended to be included within the scope of the appended claims. Although specific terms are employed herein, they are used in a generic and descriptive sense only and not for purposes of limitation. One skilled in the art will recognize many methods and materials similar or equivalent to those described herein, which could be used in the practicing the subject matter described herein. The present disclosure is in no way limited to just the methods and materials described.

What is claimed is:

1. A method of preparing a compound of Formula I,

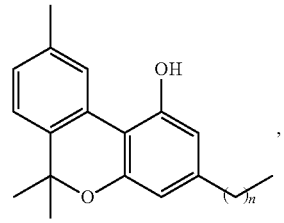

wherein, n is 1, 2, 3 or 4;
comprising,
contacting a compound of Formula II,

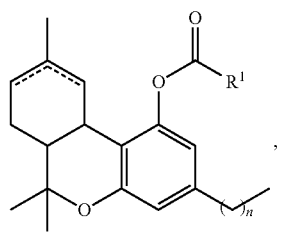

wherein,
n is 1, 2, 3 or 4; and
$R^1$ is an alkyl or aryl;
one of ------ is a double bond, the other is a single bond;
with an oxidant, optionally in the presence of a first solvent, to prepare a compound of Formula III,

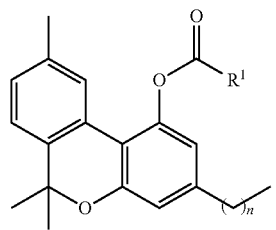

wherein,
n is 1, 2, 3 or 4; and
R¹ is an alkyl or aryl;
and,
contacting the compound of Formula III with a base in the presence of a second solvent to prepare a composition comprising a compound of Formula I.

2. The method of claim 1, wherein n is 2 or 4.

3. The method of claim 2, wherein n is 4.

4. The method of claim 1, wherein R¹ is an optionally substituted straight or branched $C_{1-6}$ alkyl selected from the group consisting of methyl, ethyl, n-propyl, isopropyl, n-butyl, sec-butyl, t-butyl, isobutyl, pentyl, neopentyl, or hexyl or an optionally substituted $C_{6-10}$ aryl selected from the group consisting of phenyl, indenyl, and napthalenyl.

5. The method of claim 4, wherein said $C_{6-10}$ aryl is naphthalenyl.

6. The method of claim 1, wherein said oxidant is present in an amount of about 1 equivalent to about 10 equivalents.

7. The method of claim 1, wherein the method does not comprise separating a compound of Formula I by column chromatography.

8. The method of claim 7, further comprising crystallizing a compound of Formula III, said crystallizing comprising, contacting the compound of Formula III with at least two crystallizing solvents to prepare a purified compound of Formula III.

9. The method of claim 8, wherein said purified compound of Formula III has a purity (AUC) of at least 80%.

10. The method of claim 8, wherein said at least two crystallizing solvents are selected from the group consisting of methanol, ethanol, isopropanol, acetone.

11. The method of claim 10, wherein said solvents are acetone and methanol.

12. The method of claim 10, wherein said solvents are in a ratio of about 1:1.

13. The method of claim 8, wherein:
n is 4;
R¹ is

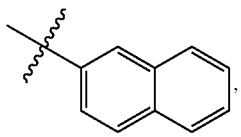 [SMILES: *c1ccc2ccccc2c1]

wherein

is the point of attachment to the carbonyl;
said first solvent is present and is toluene;
said contacting a compound of Formula II is at reflux;
said method further comprising:
filtering said compound of Formula III to prepare a first solid;
contacting said first solid with acetone (about 1 volume) and heating to about 55° C. to form a first solution;
contacting said first solution with MeOH (about 2 volumes), and heating to about 58° C. to form a second solution;
allowing said second solution to cool to about 20° C. to prepare a second solid;
filtering said second solid to prepare a filtered second solid and a filtrate;
preparing a third solid from said filtrate and re-crystallizing from acetone/methanol (about 1:1) to prepare a fourth solid;
combining said filtered second solid and said fourth solid and re-crystallizing from acetone/methanol (about 2:1) to prepare a purified compound of Formula III from said combined solids.

14. The method of 13, where said contacting the compound of Formula III with a base, comprises:
contacting the purified compound of Formula III with LiOH to prepare a compound of Formula I, having the structure:

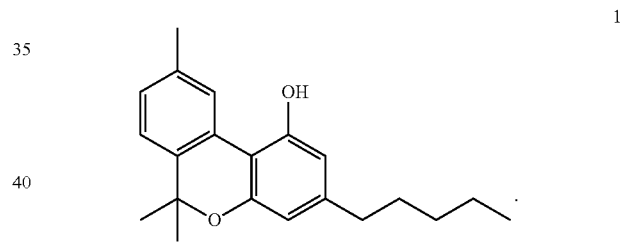

15. The method of claim 1, wherein said method is a one-pot preparation of a compound of Formula I.

16. The method of claim 15, further comprising a fractional distillation of said composition comprising a compound of Formula I to prepare a purified compound of Formula I.

17. The method of claim 16, wherein said compound of Formula I has a purity (AUC) of at least 99%.

* * * * *

UNITED STATES PATENT AND TRADEMARK OFFICE
CERTIFICATE OF CORRECTION

PATENT NO. : 12,338,223 B2  
APPLICATION NO. : 17/630221  
DATED : June 24, 2025  
INVENTOR(S) : Charla Barr et al.

Page 1 of 1

It is certified that error appears in the above-identified patent and that said Letters Patent is hereby corrected as shown below:

In the Claims

In Column 38, Line 27, Claim 14, delete "of" and insert -- of claim --, therefor.

Signed and Sealed this  
Sixteenth Day of December, 2025

John A. Squires  
*Director of the United States Patent and Trademark Office*